(12) United States Patent
Shannon et al.

(10) Patent No.: US 7,494,785 B1
(45) Date of Patent: Feb. 24, 2009

(54) RECOMBINANT SUBUNIT VACCINE

(75) Inventors: Anthony Douglas Shannon, Curtin (AU); Camilo Anthony Leo Selwyn Colaco, Trumpington (GB); Melinda Jane Frost, Ingleburn (AU)

(73) Assignee: Minister for Agriculture and Minister for Land and Water Conservation, Syndey (GB)

( * ) Notice: Subject to any disclaimer, the term of this patent is extended or adjusted under 35 U.S.C. 154(b) by 1099 days.

(21) Appl. No.: 10/049,953

(22) PCT Filed: Aug. 18, 2000

(86) PCT No.: PCT/AU00/00988

§ 371 (c)(1),
(2), (4) Date: Jun. 17, 2002

(87) PCT Pub. No.: WO01/14411

PCT Pub. Date: Mar. 1, 2001

(30) Foreign Application Priority Data

Aug. 19, 1999 (AU) .................................... PQ2337

(51) Int. Cl.
C12P 25/00 (2006.01)
(52) U.S. Cl. .................. 435/69.1; 435/320.1; 530/300; 530/350; 424/196.11; 424/197.11; 424/278.1
(58) Field of Classification Search ................ 530/300, 530/350; 435/69.1, 320.1; 424/196.11, 197.11, 424/278.1
See application file for complete search history.

(56) References Cited

U.S. PATENT DOCUMENTS

| 5,591,632 | A | 1/1997 | O'Donnell et al. |
| 5,614,381 | A | 3/1997 | Bromley et al. |
| 5,736,146 | A | 4/1998 | Cohen et al. |
| 5,747,332 | A | 5/1998 | Wallen et al. |
| 5,776,465 | A | 7/1998 | O'Donnell et al. |
| 5,789,245 | A | 8/1998 | Dubensky, Jr. et al. |
| 5,830,464 | A | 11/1998 | Srivastava |
| 5,837,251 | A | 11/1998 | Srivastava |

FOREIGN PATENT DOCUMENTS

| WO | WO 95/24923 | 9/1995 |
| WO | WO 96/37616 | 11/1996 |
| WO | WO 97/06685 | 2/1997 |
| WO | WO 97/06821 | 2/1997 |
| WO | WO 97/06828 | 2/1997 |
| WO | WO 97/10000 | 3/1997 |
| WO | WO 97/10001 | 3/1997 |
| WO | WO 97/10002 | 3/1997 |
| WO | WO 98/12208 | 3/1998 |
| WO | WO 98/23735 | 6/1998 |
| WO | WO 98/34641 | 8/1998 |
| WO | WO 98/34642 | 8/1998 |
| WO | WO 98/35705 | 8/1998 |
| WO | WO 99/02670 | 1/1999 |
| WO | WO 99/07860 | 2/1999 |
| WO | WO 99/24049 | 5/1999 |
| WO | WO 99/29384 | 6/1999 |
| WO | WO 99/31257 | 6/1999 |
| WO | WO 99/42121 | 8/1999 |
| WO | WO 99/42472 | 8/1999 |
| WO | WO 00/10597 | 3/2000 |
| WO | WO 00/20606 | 4/2000 |

OTHER PUBLICATIONS

Dirk Deregt, et al., Monoclonal antibodies to the E2 protein of a new genotype (type 2) of bovine viral diarrhea virus define thre antigenic domains involved in neutralization, Virus Research, vol. 57, pp. 171-181.*
Roman et al. Immunology 1996 vol. 88 p. 487-492.*
Barrios et al., "Mycobacterial heat-shock proteins as carrier molecules. II: The use of the 70-kDa mycobacterial heat-shock protein as carrier for conjugated vaccines can circumvent the need for adjuvants and Bacillus Clamette Guerin priming," Eur. J. Immunol., 22(6):1365-72 (1992) (abstract only).
Blachere et al., "Heat shock protein-peptide complexes, reconstituted in vitro, elicit peptide-specific cytotoxic T lymphocyte response and tumor immunity," J. Exp. Med., 186(8):1315-22 (1997).
Bruschke et al., "An experimental multivalent bovine virus diarrhea virus E2 subunit vaccine and two experimental conventionally inactivated vaccines induce partial fetal protection in sheep," Vaccine, 17(15-16):1983-91 (1999) (abstract only).
Lussow et al., "Mycobacterial heat-shock proteins as carrier molecules," Eur. J. Immunol., 21(10):2297-302 (1991) (abstract only).
Perraut et al., "Successful primate immunization with peptides conjugated to purified protein derivative or mycobacterial heat shock proteins in the absence of adjuvants," Clin. Exp. Immunol., 93(3):382-6 (1993) (abstract only).

(Continued)

*Primary Examiner*—Bruce Campell
*Assistant Examiner*—Myron G Hill
(74) *Attorney, Agent, or Firm*—Marshall, Gerstein & Borun LLP

(57) ABSTRACT

A method is provided of producing an immunogenic complex comprising a heat shock protein (hsp) coupled to a heterologous antigenic polypeptide, which method comprises: (a) expressing the antigenic polypeptide in a cell which cell has been subjected to a stimulus which causes the induction of a heat shock response in said cells; and (b) recovering the antigenic polypeptide coupled to one or more hsps from said cell or the culture medium. Also provided are immunogenic compositions comprising a heat shock protein (hsp) derived from a non-mammalian eukaryote coupled to a heterologous antigenic polypeptide which composition is capable of inducing an immune response to said antigenic polypeptide in a human or animal.

10 Claims, 4 Drawing Sheets

OTHER PUBLICATIONS

Figure 2:
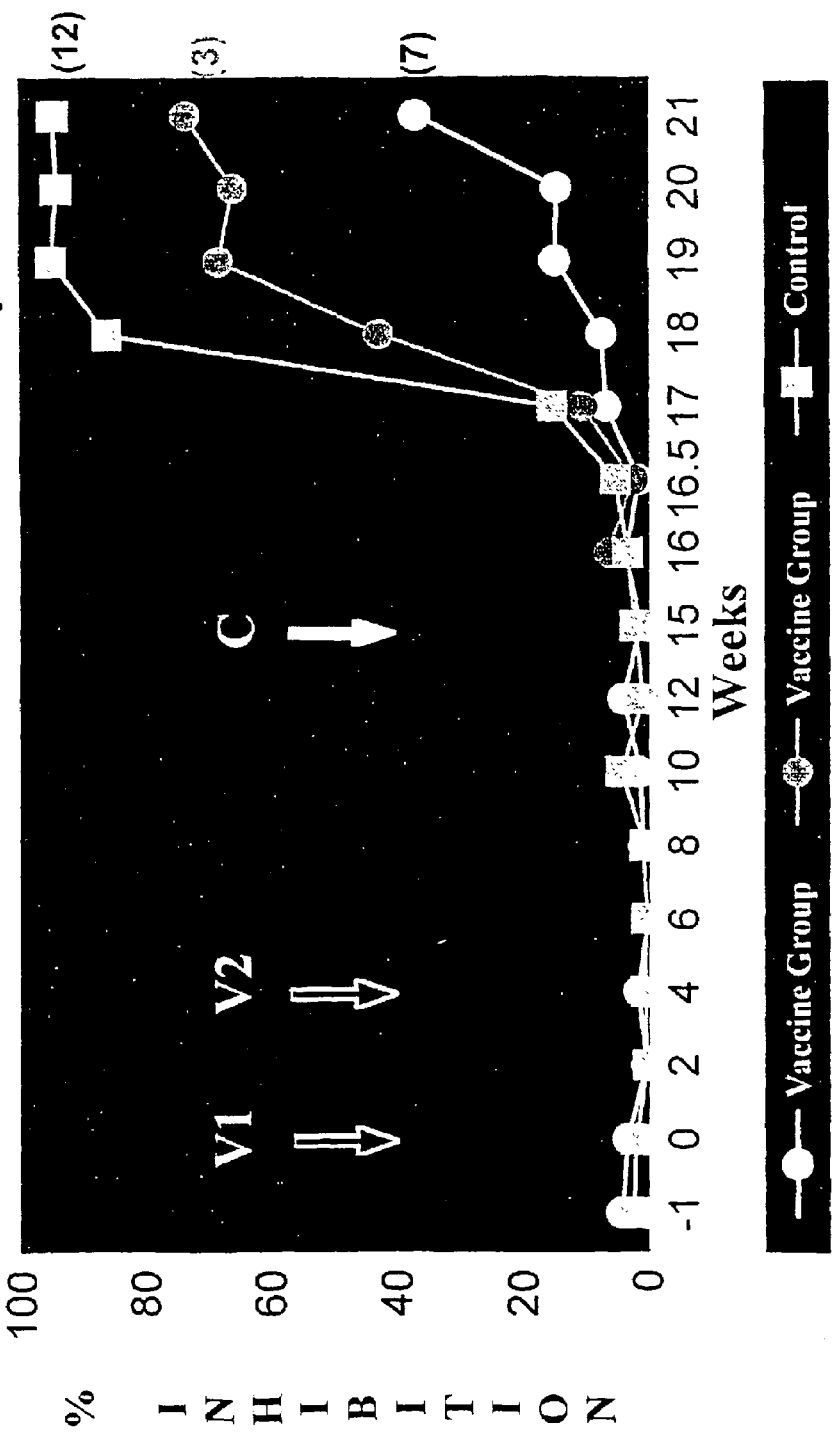

Przepiorka & Srivastava, "Heat shock protein-peptide complexes as immunotherapy for human cancer," Mol. Med. Today, 4(11):478-84 (1998) (abstract only).

Robert et al., "Phylogenetic conservation of the molecular and immunological properties of the chaperones gp96 and hsp70," Eur. J. Immunol., 31:186-95 (2001).

Srivastava & Udono, "Heat shock protein-peptide complexes in cancer immunotherapy," Curr. Op Immunol., 6:728-32 (1994).

Srivastava, et al., "Heat shock proteins come of age: primitive functions acquire new roles in an adoptive world," Immunity, 8:657-65 (1998).

Srivastava, "Purification of heat shock protein-peptide complexes for use in vaccination against cancers and intracellular pathogens," Methods, 12(2):165-71 (1997) (abstract only).

International Search Report, International Application No. PCT/AU00/00988, International Filing Date Aug. 18, 2000, Applicant Minister for Agriculture, Minister for Land and Water Conservation for and on Behalf of the State of Newsouth Wales et al.

Rico et al., "Characterization of the immunostimulatory properties of *Leishmania infanttum* HSP70 by fusion to the *Escherichia coli* maltose-binding protein in normal and nu/nu BALB/c mice," *Infection and Immunity*, 66(1):347-352 (1998).

Schirmbeck et al., "Truncated of chimeric endogenous protein antigens gain immunogenitcity for B cells by stress protein-facilitated expression," *European J. Immunol.*, 29(5): (1999).

Heikema, et al. "Generation of Heat Shock Protein-Based Vaccines by Intracellular Loading of GP96 with Antigenic Peptides," Immunology Letters, 57(1-3):69-74 (1997).

Roman et al., "Synthetic Peptides Non-Covalently Bound to Bacterial HSP 70 Elicit Peptide-Specific T-Cell Responses in Vivo" Immunology, 88(4):487-492 (1996).

Supplementary European Search Report from EP 00954158.2 mailed Apr. 13, 2006.

\* cited by examiner

Figure 1

EMAI Subunit Vaccine Trial 584/98
CTB-ELISA Anti-E2 Antibody

Figure 3

EMAI Subunit Vaccine Sheep Trial 458/99

CTB-ELISA Anti-E2 Antibody

S = Time at which the animals were slaughtered and foetuses collected.

Figure 4

EMAI Subunit Vaccine Sheep Trial 458/99

*CTB-ELISA Anti-NS3 Antibody*

RECOMBINANT SUBUNIT VACCINE

Priority is claimed to International Patent Application No. PCT/AU00/00988, filed Aug. 18, 2000, which itself claims priority to Australian Patent Application No. PQ 2337, filed Aug. 19, 1999.

FIELD OF THE INVENTION

The present invention relates generally to the field of therapeutics and the development thereof for use in animals including mammals, humans, birds and fish. More particularly, it relates to subunit vaccines that are effective against pathogens causing infections thereof for use in animals including mammals, humans, birds and fish.

BACKGROUND ART

Scientific Background

The development of therapeutics and in particular vaccines directed against pathogens such as viruses, bacteria, protozoans, fungi is ongoing. Such research has proved invaluable in preventing the spread of disease in animals including humans. In fact, in modern medicine, immunotherapy including vaccination has eradicated smallpox and virtually eradicated diseases such as polio, tetanus, tuberculosis, chicken pox, and measles.

Generally, ideal vaccines have a long shelf life, are capable of inducing long lasting immunity against a pre-selected pathogen and all of the phenotypic variants, are incapable of causing the disease to which the vaccine is directed against, are effective therapeutically and prophylactically, are easily prepared using economical standard methodologies and can be administered easily in the field.

There are four major classes of commercially available vaccines. They include non-living whole organism vaccines, live attenuated vaccines, vector vaccines, and subunit vaccines. Vaccination with non-live materials such as proteins generally leads to an antibody response or CD4+ helper T cell response while, vaccination with live materials (e.g. infectious viruses) generally leads to a CD8+ cytotoxic T-lymphocyte (CTL) response. A CTL response is crucial for protection against pathogens like infectious viruses and bacteria. This poses a practical problem, for the only certain way to achieve a CTL response is to use live agents that are themselves pathogenic. The problem is generally circumvented by using attenuated viral and bacterial strains or by killing whole cells that can be used for vaccination. These strategies have worked well but the use of attenuated strains always carries the risk that the attenuated agent may recombine genetically in the host and turn into a virulent strain. Thus, there is need for therapeutics and methods that can lead to CD8+ CTL response by vaccination with non-live materials such as proteins in a specific manner.

Subunit vaccines have provided one means for dealing with some of these problems. Such vaccines generally comprise a sub-cellular component derived from a pathogen of interest. A subunit component can be either produced from a defined sub-cellular fraction of the pathogen, be a purified protein, nucleic acid or a polysaccharide. All of these elements have an antigenic determinant capable of stimulating an immune response against the pathogen of interest. Generally, the sub-cellular component of the subunit vaccine is obtained either by purifying a preparation of disrupted pathogen or synthesised using well-known procedures.

There are, however, several limitations associated with subunit vaccines. First, a requirement for the production of such a vaccine is that the antigenic determinant(s) must be characterised and identified. This imposes limitations on their use, particularly against highly variable antigenic determinants. Second, subunit vaccines are generally ineffective in stimulating cytotoxic T cell responses. Third, the immunity conferred by subunit vaccines is often short lived and therefore requires continual booster injections. Very few recombinant expressed subunit vaccines have been shown to induce strong and long lasting immunity in vaccinated animals (including man). One notable exception is the recombinant surface antigen Hepatitis B vaccine used in man. One of the problems associated with the use of such vaccines appears to be in correctly presenting the antigens to the immune system such that strong humoral immunity and strong cell-mediated immunity are induced. In particular, existing recombinant (subunit) vaccines do not appear to result in strong 'memory' responses such that vaccinated animals react very quickly when they are exposed to natural infections caused by a pathogen.

By way of example only, deficiencies in current subunit vaccines prepared from pestiviruses like bovine viral diarrhoea virus (BVDV) have been extensively reported. These studies have shown that even though large amounts of recombinant protein were used in the vaccines, there were poor protection rates seen showing that the vaccines failed to protect from challenge with live BVDV isolates (either homologous protection or heterologous protection).

The present invention seeks to provide an improved therapeutic vaccine which ameliorates at least some of the disadvantages over existing prior art.

GENERAL BACKGROUND

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively, and any and all combinations or any two or more of the steps or features.

Although in general the techniques mentioned herein are well known in the art, reference may be made in particular to Sambrook et al., Molecular Cloning, A Laboratory Manual (1989) and Ausubel et al., Short Protocols in Molecular Biology (1999)4$^{th}$ Ed, John Wiley & Sons, Inc.

The present invention is not to be limited in scope by the specific embodiments described herein, which are intended for the purpose of exemplification only. Functionally equivalent products, compositions and methods are clearly within the scope of the invention as described herein.

Bibliographic details of the publications referred to in this specification are collected at the end of the description. All references cited are hereby incorporated by reference. No admission is made that any of the references constitute prior art.

Throughout this specification unless the context requires otherwise, the word "comprise", or variations such as "comprises" or "comprising", will be understood to imply the inclusion of a stated integer or group of integers but not the exclusion of any other integer or group of integers.

SUMMARY OF THE INVENTION

The present invention generally relates to a method of producing an immunogenic composition comprising a heat shock protein (hsp) coupled to a heterologous antigenic polypeptide, which method comprises:

(a) expressing the antigenic polypeptide in a cell which cell has been subjected to a stimulus which causes the induction of a heat shock response in said cells; and (b) recovering the antigenic polypeptide coupled to one or more hsps from said cell or the culture medium.

Preferably the cell is a non-mammalian eukaryotic cell, more preferably an insect cell. Typically, the antigenic polypeptide is expressed in the cell by the introduction into the cell of a polynucleotide encoding the antigenic polypeptide operably linked to a regulatory control sequence capable of directing expression of the polypeptide in the cell. Preferably, the polynucleotide is part of a virus or viral vector, such as a baculovirus.

The present invention also provides a composition comprising an hsp coupled to a heterologous antigenic polypeptide, the composition being produced by the method of the invention. Desirably, the composition is capable of enhancing the animal's immunocompetence against a pathogen. Preferably the hsp is derived from a non-mammalian eukarotic cell, more preferably an insect cell.

Hsps, such as insect hsps, coupled to at least an antigenic peptide/polypeptide provide an alternative therapeutic vaccine to those discussed in the background art, for stimulating an animal's immune system to elicit an immune response against foreign pathogens. While hsps have been included in therapeutic formulations, no one has, to the best of the applicant's knowledge, employed hsps from a non-mammalian eukaryote, and more particularly insect cell hsps, coupled to at least an antigenic peptide/polypeptide in the therapeutic treatment of mammals such as domestic animals and humans.

Collective features which different subunit vaccines produced using the insect cell/baculovirus embodiment of the present invention display include:

(1) The complex is completely non-infectious.

(2) The complex is safe for use in animals since baculoviruses do not infect animal cells.

(3) Therapeutics produced according to the invention will be cheaper to manufacture in that much higher yields of antigenic proteins can be produced from baculovirus-infected insect-cell cultures than from comparable systems.

(4) Therapeutics developed according to the invention have been found to generate very strong memory responses in animals. Thus when an animal is subsequently challenged with a pathogen they mount a very rapid and strong response to that pathogen.

Accordingly, the present invention also provides a composition comprising a heat shock protein (hsp) derived from a non-mammalian eukaryote coupled to a heterologous antigenic polypeptide which composition is capable of inducing an immune response to said antigenic polypeptide in a mammal.

Preferably the hsp is an insect heat shock protein. Thus in a preferred embodiment, the present invention provides an improved subunit vaccine capable of inducing an immune response in an animal comprising: an insect cell hsps coupled to an antigenic heterologous peptide or polypeptide.

Preferably, the hsp and the antigenic polypeptide are coupled by non-covalent means.

Preferably, the antigenic polypeptide is an antigen of a pathogenic organism, or an antigenic fragment or derivative thereof. More preferably the antigenic polypeptide is an antigen of a virus or bacterium, or an antigenic fragment or derivative thereof. In a preferred embodiment, the antigenic polypeptide is derived from a pestivirus such as BDVD, more particularly an E1/E2 or NS3/NS4a polypeptide or a fragment or derivative thereof.

In a highly preferred embodiment, the composition is obtainable by a method comprising:

(a) expressing the antigenic polypeptide in a non-mammalian eukaryotic cell which cell has been subjected to a stimulus which causes the induction of a heat shock response in said cells; and (b) recovering the antigenic polypeptide coupled to one or more hsps from said cell or the culture medium.

Thus, the present invention also provides methods for preparing an hsp—antigenic heterologous peptide or polypeptide complex comprising: (a) introducing into a cell a nucleotide sequence encoding at least a antigenic peptide or polypeptide(s), said nucleotide sequence being introduced into the cell in such a manner that translation of the nucleotide sequence is possible when the sequence is within the cell; (b) culturing the cell under conditions that provide for expression of the peptide or polypeptide; (c) exposing the cell to a stress that is capable of initiating the production of heat shock proteins in that cell; and (d) recovering the expressed complex. This procedure can also be accompanied by the step of: purifying the complex by any means known in the art. In a preferred embodiment, the complex produced by the method is isolated from insect cell polypeptides.

Compositions of the invention are useful in therapeutic methods for inducing an immune response against the antigenic heterologous peptide or polypeptide.

The present invention also provides a pharmaceutical composition comprising an immunogenic amount of a composition of the invention together with a pharmaceutically acceptable carrier or diluent.

In a further embodiment the invention provides a method for inducing immunocompetence in a animal against a pathogen, said method comprising the steps of: administering to an animal a therapeutically effective amount of a non-mammalian eukaryotic hsp coupled to an antigenic peptide or polypeptide and a pharmaceutically acceptable carrier.

Preferably the methods of the invention comprise methods of eliciting an immune response in an individual in whom the treatment or prevention of infectious diseases is desired by administering a composition comprising a therapeutically effective amount of a complex, in which the complex consists essentially of hsps non-covalently bound to an antigenic molecule using any convenient mode of administration. A variety of administrative techniques may be utilized, among them oral administration, nasal and other forms of transmucosal administration, parenteral techniques such as subcutaneous, intravenous and intraperitoneal injections, catheterizations and the like.

DETAILED DESCRIPTION OF THE INVENTION

The present invention is based on the finding that a recombinant subunit vaccine based on BVDV antigens expressed using a baculovirus system in insect cells that have been heat-shocked is highly effective at preventing infection of both cows and sheep by BVDV, including a challenge strain which is only distantly related to the BVDV strain whose polypeptide subunits were used as the basis of the vaccine. This is in complete contrast to previously described subunit vaccines against BVDV which do not afford broad protection against BVDV infection from a number of different strains.

This system not only results in highly efficacious vaccine composition but is also cheaper and safer than the existing alternatives.

Heat Shock Proteins and Antigenic Polypeptides

Heat shock proteins (hsps) are synthesized by a cell in response to heat shock and other forms of cellular stress. The major hsps can accumulate to very high levels in stressed cells, but they occur at low to moderate levels in cells that are not stressed. Heat shock proteins, useful in the present invention are proteins (i) whose intracellular concentration increases when a cell is exposed to a stressful stimuli, (ii) that are capable of binding other proteins or peptides, and (iii) are capable of releasing the bound proteins or peptides in the presence of adenosine triphosphate (ATP) or low pH. Particular examples of heat shock proteins suitable in the context of the present invention include some of the class of proteins termed molecular chaperones.

Chaperones, including chaperonins, are polypeptides which promote protein folding by non-enzymatic means, in that they do not catalyse the chemical modification of any structures in folding polypeptides, but promote the correct folding of polypeptides by facilitating correct structural alignment thereof. Molecular chaperones are well known in the art, several families thereof being characterised. Molecular chaperones are highly conserved between different organisms. Examples of chaperones include the hsp70 family (DnaK type), the hsp60 family (GroEL type), ER-associated chaperones, the hsp90 family, Hsc70, the HSP40 family (DnaJ), mitochondrial hsp70, mitochondrial m-AAA and yeast Ydj1. It is particularly preferred to use members of the hsp60, hsp70 and hsp90 families, whose intracellular concentration rises in response to a stress stimulus.

Heat shock proteins are found in prokaryotic cells and eukaryotic cells and when the immunogenic compositions are produced by the heat shock method of the invention, the hsps present in the hsp/antigen complex may be from any source, prokaryotic or eukaryotic. However, it is preferred that the hsps are derived from non-mammalian cells, more preferably non-mammalian eukaryotic cells such as insect cells.

Thus, typically, the hsps present in the compositions of the present invention will be derived from non-mammalian eukaryotic cells.

"Non-mammalian eukaryotic cells" are all eukaryotic cells excluding mammalian cells. For example, non-mammalian eukaryotic cells include yeast cells, fungal cells, invertebrate cells such as insect cells and non-mammalian vertebrate cells such as amphibian cells. It is preferred to use cells that allow for glycosylation of heterologous polypeptides expressed in said cells, and other post-translation modifications typically performed in the endoplasmic reticulum/golgi body of mammalian cells. However it is not necessary for the cells to carry out precisely the same post-translational modifications as would be performed in a mammalian cell. For example insect cells tend to incorporate less complex sugars into newly synthesized amino acid chains than is the case with mammalian cells.

"Non-mammalian cells" include the non-mammalian eukaryotic cells described above as well as prokaryotic cells. Prokaryotic cells include eubacteria such as *E. coli, B. subtilis* and any other bacteria suitable for the expression of heterologous polypeptides. Prokaryotic cells may be more suited for the expression of bacterial antigens rather than viral antigens. "Mammalian cells", which may be used in the method of the invention include cell lines such as CHO cells, HeLa cells and any other mammalian cell type suitable for the expression of heterologous polypeptides.

The phrase "hsp-antigenic peptide/polypeptide complex", as used herein, refers to any complex that can be isolated from a culture of cells that comprises hsps coupled to at least a heterologous peptide or polypeptide having at least one antigenic determinant. Preferably, the coupling is achieved using non-covalent bonding.

The phrase "non-mammalian hsp-antigenic peptide/polypeptide complex", as used herein, refers to any complex that can be isolated from a culture of non-mammalian cells that comprises non-mammalian hsps coupled to at least a heterologous peptide or polypeptide having at least one antigenic determinant. Preferably, the coupling is achieved using non-covalent bonding.

The term "heterologous polypeptide", as used herein, refers to a peptide or polypeptide not endogenous to the cell, such as the non-mammalian cell, i.e. not encoded by the genome of that cell. Preferably it is something not normally endogenously complexed with hsps in vivo and does not normally co-purify with hsps such as non-mammalian eukaryotic hsps.

The term "polypeptide" as used herein, refers to any amino acid sequence longer than one amino acid and thus includes peptides of two or more amino acids in length, typically having more than 5, 10 or 20 amino acids, which may or may not be modified by chemical means. The term "polypeptide" as used herein also includes proteins, a term which includes single-chain polypeptide molecules as well as multiple-polypeptide complexes where individual constituent polypeptides are linked by covalent or non-covalent means.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule.

Antigenic molecules can be selected from among those known in the art or selected by their ability to bind to antibody or MHC molecules or generate immune responses. They include any molecule that will induce an immune response against the infectious agent, e.g., antigens of viruses, bacteria, fungi, parasites etc. In a preferred embodiment of the invention the antigenic molecules may be derived from, but are not limited to: (1) viral proteins such as, proteins of any of the immunodeficiency viruses including human immunodeficiency virus type I (HIV-I) and human immunodeficiency virus type II (HIV-II), flaviviruses, pestiviruses like bovine viral diarrhoea virus (BVDV), border disease virus (BDV) and classical swine fever virus (CSFV), hepatitis type A, hepatitis type B, hepatitis type C, hepatitis type E, hepatitis type G (GB), influenza, Varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus and polio virus; (2) antigenic bacterial proteins selected from, but not limited to, mycobacteria, rickettsia, mycoplasma, neisseria and legionella; (3) antigenic protozoa proteins selected from, but not limited to, leishmania, coccidia, and trypanosoma; and (4) antigenic parasite proteins selected from, but not limited to, chlamydia and rickettsia.

It is particularly preferred to use antigenic polypeptides derived from pestivirus proteins, such as C/E0, E1/E2, NS3/NS4A and/or NS5A/B. Preferably the pestivirus is selected from BVDV (type 1 and/or type 2) and BDV.

Compositions of the invention may comprise more than one different hsp/antigenic polypeptide complex. For example, two or more different antigenic polypeptides may be used to enhance the immunogenicity of the invention. The two or more antigenic polypeptides may be derived from the same protein or from different proteins. It is particularly preferred in the case of pestiviruses to use at least one antigenic polypeptide derived from a structural protein and at least one antigenic polypeptide derived from a non-structural polypeptide. For example, in a highly preferred embodiment, a composition of the invention comprises both an hsp-pestivirus E1/E2 complex and an hsp-pestivirus NS3/NS4A complex.

Where more than one antigen is present in a composition of the invention, at least one antigenic polypeptide should be capable of providing a protective immune response when administered to a human or animal as part of an hsp complex. However, it may be desirable to include an hsp/antigenic polypeptide which does not provoke an antibody response and prevents or reduces the generation of an immune response to that particular antigen when the vaccinated host is subsequently infected by the corresponding natural pathogen. This provides a useful marker for vaccinated subjects. By way of example, a truncated BVDV NS3/NS4A antigen has been demonstrated in the Examples section to provide such a utility.

Preparation of Compositions Comprising Hsps Coupled to Antigenic Polypeptides

Compositions of the invention comprising hsps coupled to antigenic polypeptides may be made by a variety of methods.

For example, purified or partially purified non-mammalian eukaryotic hsps obtained by recombinant means, chemical synthesis and/or from natural sources such as cell lysates of non-mammalian eukaryotic cells, may be combined in vitro in a suitable vessel with one or more antigenic polypeptides, which may be obtained by recombinant means, chemical synthesis and/or from cell lysates from a suitable natural source, such as a virally-infected mammalian cell or culture of pathogenic bacteria. The hsps may be pretreated, prior to complexing with an antigenic polypeptide, with ATP or low pH to remove any peptides that may be associated with the hsps of interest. Excess ATP may be removed from the preparation by the addition of apyranase. Where low pH is used, the pH should be readjusted to neutral pH. Hsps may then be coupled to the antigenic peptide by mixing the pretreated hsp with the antigenic peptide in a suitable vessel and incubating for from 10 minutes to several hours. Typically a ratio of greater than one part antigenic peptide to one part hsp is used. Optionally, the mixture may then be purified to remove uncomplexed antigenic peptides.

In a highly preferred embodiment of the present invention, the hsp/antigenic polypeptide complexes are prepared by expressing the antigenic polypeptide in a cell under conditions whereby the stress response of the cell is induced and the intracellular levels of endogenous heat shock proteins is increased. This method is particularly convenient since it is not necessary to purify or synthesise hsps, which is advantageous when cells are used whose hsps are not well characterized. In addition, it likely that the expression of antigenic polypeptides in the intracellular environment in the presence of endogenous hsps will lead to more efficient coupling than is possible in a cell-free system.

It is preferred to use non-mammalian cells, such as non-mammalian eukaryotic cells or prokaryotic cells, more preferably non-mammalian eukaryotic cells.

Thus in a preferred method of the invention, a composition of the invention is prepared by firstly introducing a polynucleotide encoding an antigenic polypeptide of interest into a cell. The polynucleotide will comprises regulatory control sequences such as a promoter, one or more enhancers and other transcriptional/translational control sequences so as to allow for the expression of the antigenic polypeptide in the cell. It may be desirable to use regulatory control sequences that allow for inducible expression of the antigenic polypeptide, for example in response to the administration of an exogenous molecule, or indeed a stimulus such as heat shock. This will ensure that synthesis of the antigenic polypeptide does not occur until the levels of heat shock proteins have been upregulated by a heat shock stimulus. Alternatively, temporal control of expression of the antigenic polypeptide may occur by only introducing the polynucleotide into the cell when it is desired to express the polypeptide.

It may also be convenient to include an N-terminal secretion signal so that the antigenic polypeptide is secreted into the cell medium, as is the case with the E1/E2 BVDV polypeptide described in the examples.

In a preferred embodiment, the polynucleotide is part of a viral vector, such as a baculovirus vector, or infectious virus, such as a baculovirus. This provides a convenient system since not only can recombinant viral stocks can be maintained and stored until ready for use but also the delay in protein expression post-infection is known for viruses such as baculoviruses so the optimum time to shock the host cells can easily be determined and reproduced. Desirably the nucleotide sequence encoding the antigenic peptide or polypeptides is inserted into a recombinant baculovirus that has been genetically engineered to produce antigenic peptide or polypeptides, for instance, by following the methods of Smith et al (1983) *Mol Cell Biol* 12: 2156-2165. A number of viral transfer vectors allow more than one polynucleotide sequence encoding a polypeptide to be inserted into the same vector so that they can be co-expressed by the same recombinant virus.

The method of the invention is not limited to the production of one antigenic polypeptide at a time in the host cell. Multiple polynucleotides encoding different antigenic polypeptides of interest may be introduced into the same host cell. The polynucleotides may be part of the same nucleic acid molecule or separate nucleic acid molecules.

Once the polynucleotide encoding the antigenic polypeptide of interest has been introduced into the host cell, the cell is cultured under suitable conditions to provide for expression of the protein. The cells are then heat shocked to induce expression (or enhance expression of) endogenous hsps. Conditions for heat shocking cells are known in the art for a range of host cells. By way of example, specific conditions for insect cells are provided below.

Once the cells have been cultured for a suitable period to allow for protein expression, the antigenic polypeptide/hsp complexes are recovered from the cell. In this respect, the complexes may be found within the cell and/or in the cell medium. Intracellular complexes may be recovered using standard lysis and purification procedures. Secreted complexes may be recovered from the external medium and purified by procedures such as concentration using a Centricon tube. When complexes of the present invention are secreted into the medium, it is preferred to adapt the host cells to serum-free medium.

Recovered hsp-/antigenic polypeptide complexes are then typically combined with a pharmaceutically acceptable carrier or diluent and/or other components to produce pharmaceutical compositions/vaccine compositions.

Although a variety of non-mammalian eukaryotic cells, such as yeast cells, fungal cells, invertebrate cells and non-mammalian vertebrate cells may be used as host cells according to the methods of the present invention, it is preferred to use insect cells. Preferably the insect cells are derived from a Lepidopteran species, e.g. *Spodoptera frugiperda* such as the Sf9 and Sf21 cell lines.

By way of example only coupling of an antigenic proteins to insect cell hsps in vitro may be accomplished quite simply by placing infected cells (in a container), at between 24 to 48 hrs pest-infection, in a water bath at, for example, 43° C. for approximately 10 mins to heat shock the cells. The cells are then incubated at about 27.5° C. for a further 2 to 24 hrs to allow expression of coupled recombinant protein and hsps. At the end of 72 to 96 hrs in total post-infection, harvesting of the recombinant protein cultures is carried out.

The optimum periods and temperatures for inducing a heat shock response in various suitable host cells and allowing for optimum expression of the antigenic polypeptides can easily be determined by the skilled person, for example by conducting a time course, or have already been determined for many cell lines.

Typically, the heat shock response is induced after induction of the expression of the antigenic polypeptide or at about the same time, more preferably after.

Hsp/antigenic polypeptide compositions may optionally be tested for immunogenicity prior to administration to human or animal subjects using in vitro assays known in the art such as the mixed lymphocyte target culture assay (MLTC).

Compositions

Compositions of the invention comprising hsps coupled to antigenic polypeptides may preferably be combined with various components to produce compositions of the invention. Preferably the compositions are combined with a pharmaceutically acceptable carrier or diluent to produce a pharmaceutical composition (which may be for human or animal use). Compositions of the invention comprising hsps coupled to antigenic polypeptides may also be combined with suitable components to obtain vaccine compositions.

Thus, the invention provides pharmaceutical/vaccine compositions comprising a non-mammalian eukaryotic hsp-antigenic peptide or polypeptide complex that enhances the immunocompetence of the host individual and elicits specific immunity against pathogens. The therapeutic regimens and pharmaceutical compositions of the invention are described below. These compositions are believed to have the capacity to prevent the onset and progression of infectious diseases.

Generally pharmaceutical compositions and/or vaccine compositions of the invention will comprise a therapeutically effective amount of an hsp coupled to an antigenic polypeptide.

The phrase "pharmaceutically acceptable carrier or diluent" refers to molecular entities and compositions that are physiologically tolerable and do not typically produce an allergic or similarly untoward reaction, such as gastric upset, dizziness and the like, when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or soluble saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

The phrase "therapeutically effective amount" as used herein refers to an amount sufficient to stimulate by at least about 15%, preferably by at least 50%, more preferably by at least 90%, and most preferably completely, a animals immune system causing it to generate an immunological memory against the antigenic determinant.

In general, comprehended by the invention are pharmaceutical compositions comprising therapeutically effective amounts of the invention together with pharmaceutically acceptable diluents, preservatives, solubilizers, emulsifiers, adjuvants and/or carriers. Such compositions may include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present complexes. See, e.g., Martin, *Remington's Pharmaceutical Sciences*, 18th Ed. (1990, Mack Publishing Co., Easton, Pa. 18042) pages 1435-1712 which are herein incorporated by reference. The compositions may be prepared in liquid form, or may be in dried powder, such as lyophilized form.

Pharmaceutical compositions may be for administration by injection, or prepared for oral, pulmonary, nasal or other forms of administration. The mode of administration of the complexes prepared in accordance with the invention will necessarily depend upon such factors as the stability of the complex under physiological conditions, the intensity of the immune response required, the type of pathogen etc.

Preferably, the complex is administered using standard procedures, for example, intravenously, subcutaneously, intramuscularly, intraorbitally, ophthalmically, intraventricularly, intracranially, intracapsularly, intraspinally, intracisternally, intraperitoneally, buccal, rectally, vaginally, intranasally, orally or by aerosol administration.

Vaccines may also be prepared from one or more hsp/antigenic polypeptide complexes of the invention. The preparation of vaccines which contain immunogenic complexes as active ingredients, is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine.

The term "adjuvant" as used herein, refers to a compound or mixture that enhances the immune response to a composition containing an hsp coupled to a peptide or polypeptide having at least one antigenic determinant. An adjuvant can serve as a tissue depot that slowly releases the antigen and also as a lymphoid system activator that non-specifically enhances the immune response.

Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, immuno stimulating complexes (IS-COMs), liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminum hydroxide), or a mixture of Amphigen and Alhydrogel are used. Only aluminum hydroxide is approved for human use.

The proportion of immunogen and adjuvant can be varied over a broad range so long as both are present in effective amounts. For example, aluminum hydroxide can be present in an amount of about 0.5% of the vaccine mixture ($Al_2O_3$ basis). Conveniently, the vaccines are formulated to contain a final concentration of immunogen in the range of from 0.2 to 200 µg/ml, preferably 5 to 50 µg/ml, most preferably 15 µg/ml.

After formulation, the vaccine may be incorporated into a sterile container which is then sealed and stored at a low temperature, for example 4° C., or it may be freeze-dried. Lyophilisation permits long-term storage in a stabilised form.

The effectiveness of an adjuvant may be determined by measuring the amount of antibodies directed against an immunogenic complex of the invention resulting from administration of this complex in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

The complexes of the invention may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Other Active Ingredients

Compositions of the present invention may further comprise antigenic polypeptides that are not coupled to hsps and/or biologically active molecules whose primary purpose is not to serve as an antigen but to modulate the immune response in some other aspect. Examples of biologically molecules that modulate the immune system of an animal or human subject include cytokines.

The term "cytokine" refers to any secreted polypeptide that influences the function of other cells mediating an immune response. Some examples of cytokines include, but are not limited to, interleukin-1.alpha. (IL-1.alpha.), interleukin-1.beta. (IL-1.beta.), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interferon .alpha. (IFN.alpha.), interferon .beta. (IFN.beta.), interferon .gamma. (IFN.gamma.), tumor necrosis factor .alpha. (TNF.varies.), tumor necrosis factor .beta. (TNF.beta.), granulocyte colony stimulating factor (G-CSF), granulocyte/macrophage colony stimulating factor (GM-CSF), and transforming growth factor beta. (TGF-.beta.).

Therapeutic Uses

The compositions of the present invention may be used to vaccinate animals and humans against infectious diseases. The term "animal" includes: mammals such as farm animals including sheep, goats, pigs, cows, horses, llamas, household pets such as dogs and cats, and primates; birds, such as chickens, geese and ducks; fish; and reptiles such as crocodiles and alligators.

Thus, the present invention a method of inducing a protective immune response in an animal or human against a pathogen, which method comprises administering to said animal or human an effective amount of a composition of the invention.

Thus, the present invention also provides methods for enhancing an animal's immunocompetence and the activity of its immune effector cells against a pathogen. Such methods will typically include the step of: administering a composition comprising a therapeutically effective amount of an insect cell hsp-antigenic peptide/polypeptide complex, in which the complex consists essentially of an hsp coupled to an heterologous peptide or polypeptide antigenic molecule.

In a highly preferred embodiment, the present invention provides hsps complexes prepared from proteins and polypeptides derived from a pestivirus, preferably bovine viral diarrhoea virus (BVDV), more preferably BVDV E1/E2 and/or NS3/NS4A and/or antigenic fragments thereof. The hsp may be derived from any source but is preferably derived from a non-mammalian eukaryotic cell.

The term "vaccine" as used herein, refers to mean any composition of the invention containing an hsp coupled to a peptide or polypeptide having at least one antigenic determinant which when administered to a animal is capable of stimulating an immune response against the antigenic determinant. It will be understood that the term vaccine does not necessarily imply that the composition will provide a complete protective response. Rather a therapeutic effect will be sufficient.

The phrase "immune response" refers to any cellular process that is produced in the animal following stimulation with an antigen and is directed toward the elimination of the antigen from the animal. The immune response typically is mediated by one or more populations of cells characterized as being lymphocytic and/or phagocytic in nature.

The immune response generated against an introduced hsps-antigenic peptide or polypeptide complex will be dictated by the amino acid constitution of the antigenic determinants located on the peptide or polypeptide in the complex.

Such determinants may define either humoral or cell mediated antigenic regions.

Without being limited to any particular mode of action, it is contemplated that the immune response generated by the insect cell hsps-antigenic peptide or protein complex will preferably include both humoral and cell mediated immune responses. Where a cell mediated immune response is effected it preferably leads to a T cell cascade, and more specifically by means of a cytotoxic T cell cascade.

The term "cytotoxic T cell", as used herein, refers to any T lymphocyte expressing the cell surface glycoprotein marker CD8+ that is capable of targeting and lysing a target cell which bears a major histocompatibility class I (MHC Class I) complex on its cell surface and is infected with an intracellular pathogen.

Diseases that might be treated or prevented by the methods of the present invention are caused by pathogens including, but not limited to viruses, bacteria, fungi, protozoa and parasites.

Viral diseases that can be treated or prevented by the methods of the present invention include, but are not limited to, those caused by immunodeficiency viruses including human immunodeficiency virus type I (HIV-I) and human immunodeficiency virus type II (HIV-II), flaviviruses, hepatitis type A, hepatitis type B, hepatitis type C, pestiviruses like bovine viral diarrhoea virus (BVDV), Border Disease Virus (BDV) and classical swine fever virus (CSFV), influenza, Varicella, adenovirus, herpes simplex type I (HSV-I), herpes simplex type II (HSV-I), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus and polio virus.

Bacterial diseases that can be treated or prevented by the methods of the present invention are caused by bacteria including, but not limited to, mycobacteria, rickettsia, mycoplasma, neisseria and legionella.

Protozoal diseases that can be treated or prevented by the methods of the present invention are caused by protozoa including, but not limited to, leishmania, coccidia, and trypanosoma.

Parasitic diseases that can be treated or prevented by the methods of the present invention are caused by parasites including, but not limited to, chlamydia and rickettsia.

According to a highly preferred embodiment there is provided a subunit therapeutic against BVDV infections in cattle herds that is capable of inducing an immune response in cattle comprising: an hsp coupled to an antigenic BVDV peptide or polypeptide. Preferably, the hsps are non-covalently coupled to the antigenic BVDV peptide or polypeptide(s).

The primary aim of all modern pestivirus therapeutics is based on their ability to prevent the transplacental transmission of the virus thus breaking the cycle of infection in cattle herds. The foetal protection index is the only objective measurement of efficacy of BVDV vaccines. It has increasingly been adopted overseas as the demonstrated requirement for future BVDV vaccine registrations.

A surprising feature of this embodiment of the invention is that 100% protection has been observed using the vaccine prior to BVDV infections in cattle. Such protection has resulted from the unusually high levels of neutralising antibodies to BVDV after only a short exposure to the live virus challenge. The subunit vaccine provides levels of neutralising antibodies never observed before by the applicants. In addition, the subunit vaccine provides a surprisingly effective memory cytotoxic T cell response. Further, the subunit vaccine provides for the first time a 100% effective inhibition of transplacental transfer of virus from dam to foetus.

In addition to the above, vaccines produced in accordance with this embodiment of the invention have particular advantages over other BVDV vaccines and in particular BVDV subunit vaccines. One of the drawbacks of using live attenuated vaccines or whole organism vaccines is the likelihood of infection of cell cultures during manufacture of the vaccine. In contrast, subunit vaccines are non-infectious. In particular, the subunit vaccine of the invention does not require serum for manufacture, thus alleviating the risks involved with handling serum products such as foetal calf serum.

Another advantage of these vaccines is their safety when vaccinating commercial herds of animals such as cattle against BVDV. The subunit vaccine of the present invention can be used safely in animals without the risk of infection (live attenuated viruses) or infection of the animal cells with the virus. Thus it is safe to use in all animals, including pregnant animals.

A further advantage of BVDV subunit vaccines produced in accordance with the invention is the cost-effective nature of producing the subunit vaccine. It is possible to obtain high yields of antigenic proteins. In particular, in a preferred embodiment of the invention a subunit vaccine is produced using a vector baculovirus to infect insect cell cultures, producing a subunit vaccine effective against BVDV. The resulting vaccine has efficacy against a much wider range of antigenically diverse BVDV isolates.

Any antigenic region from BVDV may be used in the identified subunit vaccines. Preferably, the antigenic peptide or polypeptides are derived from the major immunogenic regions E0, E1/E2 and NS3/NS4A. In a highly preferred form of this embodiment of the invention the subunit vaccine is produced using a truncated NS3/NS4A protein from isolates of BVDV. Surprisingly, this NS3/NS4A protein antigen does not cause the production of a detectable range of antibodies in the serum of cattle vaccinated with the subunit vaccine. Thus the incorporation of the NS3/NS4A protein into the subunit vaccine provides a useful marker to distinguish infected cattle within a herd from vaccinated cattle. It is the preferred practice in Europe and the US to include a marker in the vaccine, identifying infected animals from vaccinated animals. Thus the subunit vaccine of the present invention provides an excellent marker for distinguishing infected animals within a herd from vaccinated animals.

Administration

Parenteral Delivery

The compounds provided herein can be formulated into pharmaceutical compositions by admixture with pharmaceutically acceptable nontoxic excipients and carriers and administered by any parenteral techniques such as subcutaneous, intravenous and intraperitoneal injections. In addition the formulations may optionally contain one or more adjuvants.

Oral Delivery

Contemplated for use herein are oral solid dosage forms, which are described generally in Martin, Remington's Pharmaceutical Sciences, 18th Ed. (1990 Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatised with various polymers (E.g., U.S. Pat. No. 5,013,556). A description of possible solid dosage forms for the therapeutic is given by Marshall, in Modem Pharmaceutics, Chapter 10, Banker and Rhodes ed., (1979), herein incorporated by reference. In general, the formulation will include the hsp-antigenic peptide/polypeptide complex (or a chemically modified form thereof), and inert ingredients which allow for protection against the stomach environment, and release of the biologically active material in the intestine.

Also specifically contemplated are oral dosage forms of the above derivatised hsp-antigenic peptide/polypeptide complexes. In this respect the complexes may be chemically modified so that oral delivery is efficacious. Generally, the chemical modification contemplated is the attachment of at least one moiety to the protein (or peptide) molecule itself, where said moiety permits (a) inhibition of proteolysis; and (b) uptake into the blood stream from the stomach or intestine. Also desired is the increase in overall stability of the protein and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski et al., 1981, supra; Newmark et al., J. Appl. Biochem., 4:185-189 (1982). Other polymers that could be used are poly-1,3-dioxolane and poly-1,3,6-tioxocane. Preferred for pharmaceutical usage, as indicated above, are polyethylene glycol moieties.

For the hsp-antigenic peptide/polypeptide complex the location of release may be the stomach, the small intestine (the duodenum, the jejunem, or the ileum), or the large intestine. One skilled in the art has available formulations that will not dissolve in the stomach, yet will release the material in the duodenum or elsewhere in the intestine. Preferably, the release will avoid the deleterious effects of the stomach environment, either by protection of the complex or by release of the biologically active material beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the hsp-antigenic peptide/polypeptide complex may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, alpha-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to: stearic acid including its magnesium and calcium salts, polytetrafluoroethylene (PTFE), liquid paraffin, vegetable oils and waxes. Soluble lubricants may also be used such as sodium lauryl sulphate, magnesium lauryl sulphate, polyethylene glycol of various molecular weights, and Carbowax 4000 and 6000.

Glidants that might improve the flow properties of the complex during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent. Surfactants may include anionic detergents such as sodium lauryl sulphate, dioctyl sodium sulphosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the complex either alone or as a mixture in different ratios.

Additives which potentially enhance uptake of the complex are for instance the fatty acids oleic acid, linoleic acid and linolenic acid.

Controlled release formulation may be desirable. The complex could be incorporated into an inert matrix which permits release by either diffusion or leaching mechanisms i.e., gums. Slowly degenerating matrices may also be incorporated into the formulation. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film-coated tablet; the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Pulmonary Delivery

Also contemplated herein is pulmonary delivery of the complex. The hsp-antigenic peptide/polypeptide complex may be delivered to the lungs of an animal while inhaling and traverses across the lung epithelial lining to the blood-stream.

Contemplated for use in the practice of this invention are a wide range of mechanical devices designed for pulmonary delivery of therapeutic products, including but not limited to nebulizers, metered-dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colorado; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of the complex. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modification or the type of device employed.

Formulations suitable for use with a nebulizer, either jet or ultrasonic, will typically comprise the complex suspended in water at a concentration of about 0.1 to 25 mg of biologically active protein per ml of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the complex suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the complex and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 microns, most preferably 0.5 to 5 microns, for most effective delivery to the distal lung.

Nasal Delivery

Nasal delivery of the complex is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Administration with Other Compounds

The therapeutic regimens and pharmaceutical compositions of the invention may be coadministered with additional immune response enhancers or biological response modifiers including, but not limited to, the cytokines IFN-.alpha., IFN-.gamma., IL-2, IL-4, IL-6, TNF, or other cytokine-affecting immune cells. In accordance with this aspect of the invention, the complexes of the hsp and antigenic molecule are administered in combination therapy with a therapeutically active amount of one or more of these cytokines. As used herein, the term "cytokine" is meant to mean any secreted polypeptide that influences the function of other cells mediating an immune response. Accordingly, it is contemplated that the complex can be coadministered with a cytokine to enhance the immune response directed against the tumor. Preferred cytokines include, but are not limited to, interleukin-1.alpha. (IL-1.alpha.), interleukin-1.beta. (IL-1.beta.), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interferon .alpha. (IFN.alpha.), interferon beta. (IFN.beta.), interferon gamma. (IFN.gamma.), tumor necrosis factor alpha. (TNF-.varies.), tumor necrosis factor beta. (TNF.beta.), granulocyte colony stimulating factor (G-CSF), granulocyte/macrophage colony stimulating factor (GM-CSF), and transforming growth factor beta. (TGF-.beta.).

In addition, conventional antibiotics may be coadministered with the stress protein-peptide complex. The choice of suitable antibiotics will however be dependent upon the disease in question.

Dosages

For all of the above molecules, as further studies are conducted, information will emerge regarding appropriate dosage levels for treatment of various conditions in various patients, and the ordinary skilled worker, considering the therapeutic context, age and general health of the recipient, will be able to ascertain the proper dosage.

Typically, the complex should be administered in an amount sufficient to initiate in the animal an immune response against the pathogen following subsequent challenge. The amount of insect cell hsp-antigenic peptide/polypeptide complex administered preferably is in the range of about 0.1-1.0 micrograms of complex/kg body weight of the animal/administration, and most preferably about 0.2 to 0.5 micrograms of complex/kg body weight of the animal/administration.

It is contemplated that a typical dose will be in the range of about 0.5 to about 50 micrograms for a human subject weighing about 75 kg. In addition, it is contemplated that the strength of the immune response may be enhanced by repeatedly administering the complex to the individual. Thus in one example the animal may receive at least two doses of the insect cell hsp-antigenic peptide/polypeptide complex at approximately monthly intervals. If necessary, the immune response may be boosted at a later date by subsequent administration of the complex. It is contemplated, however, that the optimal dosage and immunization regimen may be found by routine experimentation by one skilled in the art.

Kits

The invention also provides kits for carrying out the therapeutic regimens of the invention. Such kits comprise in one or more containers therapeutically or prophylactically effective amounts of the insect cell hsp-antigenic peptide/polypeptide complex in pharmaceutically acceptable form. The hsp-antigenic molecule complex in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of hsp-antigenic molecule complexes by a clinician or by the patient.

BEST MODE(S) FOR CARRYING OUT THE INVENTION

Further features of the present invention are more fully described in the following non-limiting Figures and Examples. It is to be understood, however, that this description is included solely for the purposes of exemplifying the present invention. It should not be understood in any way as a restriction on the broad description of the invention as set out above. In the drawings:

FIG. 1 The development of anti-E2 (neutralising) antibody concentration in both vaccinated (-○-) and control (-■-) groups of heifers before and after live virus challenge (C).

FIG. 2 The development of anti-NS3 antibody concentration in both the vaccinated (-○-) and control (-■-) groups of heifers before and after virus challenge (C).

FIG. 3 The development of anti-E2 (neutralising) antibody concentration in both vaccinated (-○-) and control (-■-) groups of sheep before and after live virus challenge (C).

FIG. 4 The development of anti-NS3 antibody concentration in both the vaccinated (-○-) and control (-■-) groups of sheep before and after virus challenge (C).

Methods of molecular cloning, and protein chemistry methods that are not explicitly described in the following Examples are reported in the literature and are known by those skilled in the art. General texts that described conventional molecular biology, microbiology, and recombinant DNA techniques within the skill of the art, included, for example: Sambrook et al. (1989); Glover (1985); and Ausubel, et al. *Current protocols in molecular biology*.

EXAMPLE 1

Production of Recombinant Baculoviruses and Expression of Recombinant Pestivirus Proteins Pestiviruses Pestivirus isolates Trangie-D10, Bega and Clover Lane were isolated and characterised at the Virology Department, Elizabeth Macarthur Agricultural Institute (EMAI). The BVDV isolates Trangie D10 and Bega represent Bovine Viral Diarrhoea Virus (BVDV) Type 1 pestiviruses, while the Clover Lane isolate is a Border Disease Virus (BDV) isolate.

The GenBank accession numbers of the Australian virus isolates used in the subunit vaccine and the relative positions of the genomic fragments used relative to the reference strain BVDV NADL (Accession number M31182) were as follows: Bega (AF049221) E0 partial sequence codes relative to the whole virus genome from 1171-1897; Trangie (AF049222) E0 partial sequence codes relative to the whole virus genome from 1171-1897; Bega (AF049225) E1 and E2 partial sequence codes relative to the whole-virus genome, from 2253-3490; Trangie (AF049223) E1 and E2 partial sequence codes relative to the whole virus genome, from 2290-3490; Clover Lane (AF037405, Becher et al., 1998) E1 and E2 partial sequence codes relative to the whole virus genome, from 2360-3510; Bega (AF052303) NS3, NS4a partial sequence codes relative to the whole virus genome, from 5416-7591; Trangie (AF052304) NS3, NS4a partial sequence codes relative to the whole virus genome, from 5675-7528.

Extraction of Viral RNA cDNA was transcribed from Australian BVDV isolates for all of the major immunogenic regions (E0, E1/E2 and NS3/NS4A) using standard techniques. Briefly, viral RNA was extracted from infected cells and/or viral pellets using either RNAzol (Biotex Laboratories, Inc) or TRIzol® Reagent (Gibco BRL), according to the manufacturer's instructions. Dried RNA pellets were reconstituted in 10 µl or 20 µl sterile Diethyl pyrocarbonate (DEPC) (Sigma) treated water (Sambrook et al., 1989).

Reverse Transcription to Produce cDNA for E1/E2, NS3 and E0 Immunogenic Regions cDNA was produced for E1/E2 by reverse transcription by preparing an E1/E2 reverse transcriptase (RT) mixture as described in Table 1. Tubes were heated in an FTS-960 Thermal Sequencer (Corbett Research) at 37° C. for 50 mins, followed by 70° C. for 10 mins to denature the reverse transcriptase. The RT mix was cooled at 5° C. for 2 mins prior to cDNA amplification by polymerase chain reaction (PCR).

cDNA for NS3 was also prepared by RT by preparing a NS3 RT mixture according to Table 2. Tubes were heated in an FTS-960 Thermal Sequencer at 37° C. for 59 mins, followed by 94° C. for 15 mins to denature the reverse transcriptase prior to cDNA amplification by PCR.

cDNA for E0 was produced by preparing a RT mixture as described in Table 3. Tubes were heated in an FTS-960 Thermal Sequencer at 37° C. for 50 mins, followed by 70° C. for 10 mins to denature the reverse transcriptase. The RT mix was then cooled at 5° C. for 2 mins prior to cDNA amplification by PCR.

TABLE 1

| Reagent | Volume | Final concentration | Supplier |
| --- | --- | --- | --- |
| X10 PCR buffer [100 mM Tris-HCl; 15 mM MgCl2; 500 mM KCl; pH 8.3] | 2.0 μL | X1 [10 mM Tris-HCl; 1.5 mM MgCl2; 50 mM KCl; pH 8.3] | Boehringer Mannheim |
| 25 mM MgCl$_2$ | 2.8 μL | 3.5 mM | Sigma molecular biology grade |
| dinucleotide triphosphate (dNTP) containing 5 mM each dATP, dGTP, dCTP and dTTP | 4 μl | 1 mM of each dNTP | Boehringer Mannheim |
| random hexamers (50 μM in 10 mM Tris-HCl, pH 8.3;) | 1 μl | 2.5 μM | Perkin Elmer |
| RNase-inhibitor | 10 units | — | Boehringer Mannheim |
| M-MLV | 12.5 units | — | Gibco BRL |
| RNA preparation | 1 μL | — | — |
|  | 20 μl | — | — |

TABLE 2

| Reagent | Volume | Final concentration | Supplier |
| --- | --- | --- | --- |
| X5 first strand buffer (250 mM Tris-HCl, pH 8.3; 375 mM KCl; 15 mM MgCl$_2$) | 4 μL | X1 (50 mM Tris-HCl, pH 8.3; 55 mM KCl; 3 mM MgCl$_2$:) | Gibco BRL |
| 0.1M DTT (dithiothreitol) | 2 μL | 0.01 m | Gibco BRL |
| dinucleotide triphosphate (dNTP) solution (containing 5 mM each dATP, dGTP, dCTP and dTTP), | 2 μL | 0.5 Mm | Boehringer Mannheim |
| random hexamers (50 μM in 10 mM Tris-HCl, pH 8.3) | 1 μL | 2.5 μM | Perkin Elmer |
| RNase-inhibitor | 20 units | — | (Boehringer Mannheim) |
| Superscript ™ II (RNase H⁻ Reverse Transcriptase) | 50 or 100 units | — | Gibco BRL |
| RNA preparation Heated to denature at 65° C. for 5 mins and cooled rapidly on ice before use | 1 μL | — | — |
| Total volume | 20 μL | — | — |

TABLE 3

| Reagent | Volume | Final concentration | Supplier |
| --- | --- | --- | --- |
| X10 PCR buffer [100 mM Tris-HCl; 15 mM MgCl$_2$; 500 mM KCl; pH 8.3] | 2.0 μL | X1 [10 mM Tris-HCl; 1.5 mM MgCl$_2$; 50 mM KCl; pH 8.3] | Boehringer Mannheim |
| 25 mM MgCl$_2$ | 2.8 μL | 3.5 mM | Sigma molecular biology grade |
| dinucleotide triphosphate (dNTP) containing 5 mM each dATP, dGTP, dCTP and dTTP | 4 μl | 1 mM of each dNTP | Boehringer Mannheim |
| random hexamers (50 μM in 10 mM Tris-HCl, pH 8.3; | 1 μl | 2.5 μM | Perkin Elmer |
| RNase-inhibitor | 10 units | — | Boehringer Mannheim |
| M-MLV | 12.5 units | — | Gibco BRL |
| RNA preparation | 1 μl | — | — |
|  | 20 μl | — | — |

PCR Oligonucleotide Primers

PCR primers for the BVDV isolates, Trangie and Bega, were based on conserved regions of the published sequences for overseas pestivirus isolates. The primers for the BDV isolate, Clover Lane, were made using its published sequence (Becher et al., 1998). Primers were designed using the computer programme 'Primer Designer—Version 2.0' (Scientific and Educational Software, 1990, 1991) and contained restriction sites incorporated to enable directional cloning of the cDNA (Tables 4 and 5).

Amplification of cDNA by Polymerase Chain Reaction

The amplification of cDNA from E1/E2, NS3/NS4A and E0 followed a similar procedure. The amplification reaction was carried out in a total volume of 100 µl . To the 20 µl of RT, 8 ml×10 PCR buffer (100 mM Tris-HCl; 15 mM $MgCl_2$; 500 mM KCl; pH 8.3: Boehringer Mannheim), 7.2 ml 25 mM $MgCl_2$ (to give a final concentration of 3.3 mM $MgCl_2$; Sigma, molecular biology grade), 2.5 units Taq DNA polymerase (Boehringer Mannheim) and 1 µl each of the sense and antisense primers (30 pmol per ml) were added.

E1/E2 cDNA was initially denatured at 95° C. for 2 mins, followed by 35 cycles of denaturation at 95° C. for 30 secs, annealing at 55° C. for 30 secs and extension at 72° C. for 1 min. A final extension step of 72° C. for 5 mins was included, before cooling the tubes to 5° C. for 2 mins.

TABLE 4

| Pestivirus Protein | Primer sequence[a] | Location of primer in NADL sequence[h] |
|---|---|---|
| Trangie E1/E2[b]* | 5'-CGCGGATCCAGTGCTGGCATTTGAAGA-3' (SEQ ID NO. 1) Bam HI | 2290 |
| Bega E1/E2[c]* | 5'-CGCGGATCCCAGACTGGTGGCCTTATGA-3' (SEQ ID NO. 2) Bam HI | 2253 |
| CloverLane E1/E2[d]* | 5'-CACGGATCCAGTGCATCAACAACAGCCT-3' (SEQ ID NO. 3) Bam HI | 2360 |
| Trangie E0[e]♦ | 5'-CGCGGATCCAGTTTTGTTTCAAGTTACAATG-3' (SEQ ID NO. 4) Bam HI | 1171 |
| Bega E0[f]♦ | 5'-CGCGGATCCAGTTTTGTTTCAAGTTACAATG-3' (SEQ ID NO. 5) Bam HI | 1171 |
| Trangie NS3/NS4A[g]♠ | 5'-AACTGCAGACTAGAGTGGTTTGCCAAAGCAACA-3' (SEQ ID NO. 6) Pst I | 5675 |

[a]Restriction enzyme sites are shown in bold,
[b]GenBank accession number is AF049223,
[c]GenBank accession number is AF04925,
[d]GenBank accession number is AF037405 Becher et al. (1998),
[e]GenBank accession number is F049222,
[f]GenBank accession number is Af049221,
[g]GenBank accession number is AF052304,
[h]GenBank accession number is M31182 Collett et al. (1988),
*E1/E2 fragments code for a protein containing 69 amino acids (aa) from E1 and finishing 35 aa before the end of E2,
♦codes for the full length E0 protein,
♠codes for NS3 protein without the serine protease enzyme and includes the area coding for a T-cell epitope found in CSFV (Pauly et al., 1995).

TABLE 5

| Pestivirus Protein | Primer sequence[a][b] | Location of primer in NADL sequence[i] |
|---|---|---|
| Trangie E1/E2[c]* | 5'-GCGAAGCTTAGGACTCTGCGAAGTAATC-3' (SEQ ID NO. 7) Hind III Stop | 3490 |
| Bega E1/E2[d]* | 5'-CATGCCATGGTTAGGACTCTGCGAAGTAATC-3' (SEQ ID NO. 8) NcoI Stop | 3490 |
| CloverLane E1/E2[e]* | 5'-CGCAAGCTTACGCTACCACTGCCAACATGA-3' (SEQ ID NO. 9) Hind III Stop | 3510 |
| Trangie E0[f]♦ | 5'-CGCAAGCTTAGACATCACAGTAAGGGGA-3' (SEQ ID NO. 10) Hind III Stop | 1897 |
| Bega E0[g]♦ | 5'-CGCAAGCTTAGACATCACAGTAAGGGGA-3' (SEQ ID NO. 11) Hind III Stop | 1897 |
| Trangie NS3[h]υ | 5'-ACGTCCATGGTTAAGCTTGATAGCCTACGTACC-3' (SEQ ID NO. 12) NcoI Stop | 7528 |

[a]Restriction enzyme sites are shown in bold,
[b]In frame stop codon is underlined in the anti-sense primer,
[c]GenBank accession number is AF049223,
[d]GenBank accession number is AF049225,
[e]GenBank accession number is AF037405 Becher et al. (1998),
[f]GenBank accession number is AF049222,
[g]GenBank accession number is AF049221,
[h]GenBank accession number is AF052304,
[i]GenBank accession number is M31182 Collett et al. (1988),
*E1/E2 fragments code for a protein containing 69 amino acids (aa) from E1 and finishing 35 aa before the end of E2,
υcodes for the full length E0 protein,
♦codes for NS3 protein without the serine protease enzyme and includes the area coding for a T-cell epitope found in CSFV (Pauly et al., 1995).

The Clover Lane (BDV) PCR mix did not require MgCl$_2$ and only 1 unit of Taq DNA polymerase was needed for amplification.

E0 amplification was carried out as described for E1/E2, with the exception that the initial denaturing step was at 94° C. for 2 mins.

Amplification of NS3 cDNA was carried out in a total volume of 50 µl using the total 20 µl from the reverse transcription reaction, to which was added 3 µl×10 PCR buffer (100 mM Tris-HCl-15 mM MgCl$_2$; 500 mM KCl; pH 8.3: Boehringer Mannheim), 2 µl 25 mM MgCl$_2$ (to give a final concentration of 3 mM MgCl$_2$; Sigma, molecular biology grade), 1-2 units Taq DNA polymerase (Boehringer Mannheim) and 1 µl each of the sense and antisense primers (25-30 pmol per ml). An initial denaturing step at 94° C. for 3 min was followed by 30 cycles of denaturation at 94° C. for 30 sec, annealing at 55° C. for 30 sec and extension at 72° C. for 2 min. A final extension step of 72° C. for 5 min was included, before cooling the tubes to 4° C.

Cloning of PCR Fragments

PCR products were purified with PCR SPINCLEAN™ columns (Progen Industries, Limited), according to the manufacturer's instructions. If the PCR reaction produced non-specific bands in addition to the required product, or subcloning from another plasmid was necessary, the DNA was further purified by elution from a 0.8% agarose gel, using a modification of the method described by Heery (1990).

Purified PCR fragments were digested and ligated into pBlueBacHis A, B or C baculovirus transfer vectors (MaxBac Baculovirus Expression System, Invitrogen Corporation) containing compatible cohesive overhangs, using standard cloning protocols (Sambrook et al., 1989; Current Protocols in Molecular Biology, 1991). A, B or C vectors provide three different reading frames to achieve protein expression in the baculovirus expression system (Table 6).

TABLE 6

| Pestivirus Protein | pBlueBacHis A, B or C transfer vector |
|---|---|
| Trangie E1/E2 | C |
| Bega E1/E2 | C |
| Clover Lane E1/E2 | A |
| Trangie E0 | B |
| Bega E0 | B |
| Trangie NS3/NS4A | B |

NS3/NS4A proved difficult to clone directly into the pBlueBacHis baculovirus transfer vector and was thus first cloned into pCR™ II plasmid (Invitrogen Corporation) using the Invitrogen TA Cloning Kit. The methods for this procedure were carried out according to the manufacturer's instructions. The NS3 fragment was then sub-cloned into the pBlueBacHis B vector as described for the other fragments of the genomes.

Transformation of Baculovirus Plasmids with the PCR Fragments

The ligations were transformed into competent *E. coli* strain Top 10 (Invitrogen Corporation), Genotype: F⁻mcrA D(mff-hsdRMS-mcrBC) f80lacZDM15 DlacX74 deoR recA1 araD139 D(ara-leu)7697 galU galK rpsL endA1 nupG, and/or Sure® *E. coli* (Stratagene), Genotype: e14⁻(McrA⁻)D (mcrCB-hsdSMR-mrr) 171 endA1 supE44 thi-1 gyrA96 rel A1 lac recB recJ sbcc umuc::Tn5 (kan$^r$) uurC[F' proAB lacI$^q$Z D m15 Tn10(Tet$^r$)]$^c$. Protocols for the preparation of competent cells and transformation of the bacteria were taken from the Invitrogen MaxBac Baculovirus Expression System Manual Version 1.8.

Screening Bacterial Clones for Plasmid Containing PCR Fragment and Plasmid Purification for Transfection Bacterial clones containing pBlueBacHis+PCR fragment were identified by growing colonies, extracting the plasmids using the boiling miniprep method described in Sambrook, et. al. (1989), and then undertaking restriction digests of the plasmids to verify those containing the correct-sized insert. Recombinant plasmids were purified to a level suitable for transfection reactions using plasmid purification kits (QIAGEN Pty Ltd., tip-20 or tip-100 columns), according to the manufacturer's instructions.

Production of Purified Recombinant Baculoviruses by Cationic Liposome Transfection of Sf9 Cells to Produce Recombinant Baculoviruses Recombinant baculoviruses were produced by co-transfecting linearised wild-type *Autographa californica* nuclear polyhedrosis virus (AcMNPV) DNA and baculovirus transfer vector containing PCR fragment into Sf9 cells, by the technique of cationic liposome mediated transfection. This was carried out according to the Invitrogen MaxBac Baculovirus Expression System Manual Version 1.8. Some minor modifications were made in relation to volumes, but these were not significant in terms of the overall strategy used.

Plaque Purifying Recombinant Baculoviruses

Recombinant virus was plaque purified three times before virus master stocks were prepared, ensuring the virus was cloned from a single particle and no wild-type virus was present. Plaque assays were set up according the Invitrogen MaxBac Baculovirus Expression System Manual Version 1.8.

After each round of plaque purification, the recombinant viruses were screened using a modified Pestivirus antigen-capture ELISA (PACE) (Shannon et al., 1991). The modified method involved supernatant+cells (50 µl/well) being added directly to a blocked, washed ELISA plate, and the plate incubated for 1 hr at 37° C. Antibody solution (50 µl/well) was then added. The antibody used was either biotinylated goat anti-pestivirus antiserum or individual anti-E2 or anti-NS3 monoclonal antibodies (mAbs). The plate was incubated overnight at 22° C., then developed as described by Shannon et al. (1991), omitting the incubation with biotinylated anti-mouse IgG for samples that were reacted with the biotinylated goat antiserum. It should be noted that recombinant, baculovirus-expressed E0 has not been detected in the PACE.

Recombinant Baculovirus Master, Seed and Working Stocks

The master virus stock for each of the recombinant baculoviruses constructed was made according the Invitrogen MaxBac Baculovirus Expression System Manual Version 1.8. The titre of the stock was determined by a plaque assay, as described above, except that the cells were overlaid with 1.5% carboxymethylcellulose (CMC, BDH; 6% CMC in deionised water, diluted 1 in 4 with complete TC100+X-gal [125 µg/ml, Boehringer Mannheim]). After 7 days, the blue plaques were counted to give the virus titre.

The seed and working stock were made from the master and seed stock, respectively using a low MOI of 0.1 to 0.5 pfu/ml. All virus stocks were stored at 4° C. for use in vaccine production. For long term storage of Master, Seed and Working stocks, each recombinant virus was ampouled and frozen at −80° C.

Optimisation of Recombinant Protein Production

Sf9 insect-cell suspensions, adapted to Sf-900 II Serum Free Media according to the protocol described by Gibco BRL (1995), were used to optimise recombinant protein expression. Two conical flasks, containing 50 ml cells ($1.5\times10^6$ cells per ml), were infected with recombinant baculovirus at a high and low MOI, between 0.1 and 5.0. A third flask acted as an uninfected control culture. The 3 flasks were incubated with shaking at 28° C., and 5 ml aliquots removed at 24 hr intervals for up to 7 days.

The samples were centrifuged at room temperature (RT) for 10 min at 900×g, and the supernatants carefully removed. The pellets and supernatants were stored at −20° C. until daily sampling was completed. The amount of specific, recombinant pestivirus protein in the samples was then determined using the modified PACE described above. The cell pellets were reconstituted in 200 μl or 250 μl NP-40 (1% [v/v] in PBS), vortexed and centrifuged at RT for 10 min at 900×g. Serial dilutions of the pellet extract (in 1% [v/v] NP40) were assayed. The culture supernatants were assayed undiluted, as well as serially diluted (in 1% [v/v] NP40).

It was found that the cell viability was reduced at the higher rate of infection. Therefore, an MOI or 0.1 to 2 was more appropriate. Data for the optimised expression times and the recombinant protein location in the insect-cell suspension cultures, either supernatant or pelleted-cell fraction are shown in Table 7.

TABLE 7

| Recombinant protein | Time to harvest after infection (Hours) | Recombinant protein location in infected cultures |
|---|---|---|
| Trangie E1/E2 | 48 | Supernatant |
| Bega E1/E2 | 48 | Supernatant |
| Clover Lane E1/E2 | 48 | Supernatant |
| Bega E0 | 48[a] | Supernatant + cells[b] |
| Trangie E0 | 48[a] | Supernatant + cells[b] |
| Trangie NS3/NS4A | 48 | Cells only |

[a]These proteins could not be detected in the PACE, therefore the time to harvest was based on the times at which the other recombinant proteins were harvested.

[b]Both supernatant and cells need to be harvested since the location in the insect cell suspension cultures could not be accurately determined.

In relation to the expressed E1/E2 proteins, the hydrophobic 'tail' region of this protein was deliberately omitted when constructing the cDNA of the genome encoding this region and therefore in preparing the recombinant baculoviruses responsible for protein expression in the insect-cell cultures. This resulted in the majority of these proteins being transported from the insect cells via normal protein-export pathways and secretion into the cell culture medium. Therefore, maximum protein recovery was from the supernatant fraction of the insect-cell cultures.

In contrast, the expressed NS3/NS4A protein remains 'bound' within the insect cells and therefore were harvested from pelleted cells at the end of the culture time. Cells were pelleted on a bench centrifuge at 2000×g for 10 mins, which maximised the harvest of this recombinant protein in a small volume. In the case of the E0 ($E^{ms}$) recombinant, expressed proteins, the location of these could not be determined and, therefore, culture supernatant plus insect cells were harvested.

EXAMPLE 2

Coupling of Immunogenetic BVDV Proteins to Insect Cell hsps In Vitro

The insect cells used throughout the example were *Spodoptera frugiperda* 9 (Sf9) cells (Invitrogen Corporation, USA).

Establishing Sf9 Insect Cells in Monolayers

This method was based on the Invitrogen MaxBac Baculovirus Expression System Manual, Version 1.8. Frozen cell aliquots (normally 1.0 ml vials stored in a liquid Nitrogen tank) were thawed rapidly at 37° C., the vial wiped with 70% (v/v) ethanol and the cells transferred to a 75 $cm^2$ tissue culture flask containing 15 ml complete TC100 medium (Gibco BRL TC100, supplemented with 10% FCS [Trace Biosciences Pty Ltd] and containing penicillin and streptomycin [100 units/ml each]) at room temperature (RT).

After the flask had been incubated for 1 hr at 28° C. (Clayson Incubator, Edwards Instrument Company) to allow the cells to attach, the medium was replaced with 20 ml fresh, complete TC100. The medium was changed every 48 hrs until the cells were confluent, at which stage they were passaged as follows. The medium was removed and replaced with 5 ml fresh medium, the cells gently scraped off the bottom of the flask, and 1 ml of cell suspension was transferred to a new 75 $cm^2$ tissue culture flask containing 19 ml of complete TC100 at RT. After rocking the flask to distribute the cells evenly across the bottom, the flask was placed at 28° C. and the cells grown as described above.

Culture of Sf9 Insect Cells in Suspension

This method was based on the Invitrogen MaxBac Baculovirus Expression System Manual, Version 1.8. Cells were grown as suspension cultures after they had been passaged 3-4 times as a monolayer culture. The medium used for these cultures was complete TC100 containing 1% (v/v) pluronic F-68 (10% solution; Gibco BRL). To produce the suspension cultures, medium was first removed from the cells which were a confluent monolayer and immediately replaced with 5 ml of fresh medium. The cells were gently scraped from the bottom of the flask and the cell suspension transferred to a 100 ml, screw-topped, conical flask containing 25 ml of medium containing pluronic. The flask was incubated at 28° C., shaking on an orbital shaker (Bio-Line; Edwards Instrument Company) for at least 1 hr at 80 rpm before increasing the shaking speed to 110 rpm for the remainder of the growth period. When the cell density had reached approximately $2\times10^6$ cells/ml, an additional 30 ml of medium was added. Cells were then grown on in 50 ml volumes and passaged when the cell density reached approximately $2\times10^6$ cells/ml. At this time, cells were diluted in medium to give approximately $0.5\times10^6$ cells/ml, and incubated at 28° C., shaking at 110 rpm, until passaged again.

Adaptation of Sf9 Insect Cells to Grow in Suspension Culture in Serum-Free Medium Insect cells were adapted to grow in suspension culture in serum-free medium according to the protocol described by Gibco BRL (1995). Cells that had been growing in complete TC100 with pluronic were transferred to 50 ml of serum-free medium (Sf-900 II SFM; Gibco BRL) containing penicillin and streptomycin (100 units/ml each) at a density of $5\times10^5$ cells/ml. The cells were grown on to a density of $2\times10^6$ cells/ml, then passaged at a density of $5\times10^5$ cells/ml. This was continued until a cell density of $2\times10^6$ cells/ml, with a cell viability of at least 80%, was reached. The cells were then considered to be adapted to grow in serum-free medium, and subsequently were passaged using serum-free medium in the same way as described for cells grown in complete TC100 medium with pluronic F-68, as described for the culturing of Sf9 insect cells in suspension.

Requirements for Sf9 Cells Used to Express Recombinant Pestivirus Proteins

Sf9 cells in serum-free medium, used for the expression of recombinant pestivirus proteins, were required to be below 30 passages in culture. Conical flasks (500 ml) were seeded with Sf9 cells at a density $0.5\times10^6$ cells/ml in a final volume of 150 ml. When the cells in these flasks reached a density of 1.0–$1.5\times10^6$ cells/ml, they were infected with the appropriate recombinant baculovirus encoding the required, expressed pestivirus protein.

Production of the Recombinant Baculoviruses Encoding Pestivirus Proteins

Production of recombinant baculoviruses and expression of recombinant pestivirus proteins is described in Example 1.

Multiplicity of Infection

The Sf9 insect cells were infected at a multiplicity of infection (MOI) ranging between 0.1 and 2.0, depending on the individual recombinant-baculovirus stock titre. Results are shown in Table 8.

Induction of Heat Shock Proteins in Cultures of Sf9 Cells Infected with Recombinant Baculoviruses The experimental times and temperatures used to induce the production of heat shock proteins in insect-cell cultures were optimised for Sf9 insect-cell cultures expressing specific pestivirus recombinant proteins, as set out below.

Heat Shock Conditions for NS3/NS4A Recombinant Baculovirus-Infected Cultures

Sf9 insect cells infected with the recombinant baculovirus expressing the truncated pestivirus NS3/NS4A protein were incubated at 28° C., with shaking at 110 rpm, for 48 hours. The infected cell cultures flasks were then placed in a 43° C. water bath along with a similar 'dummy' cell culture flask containing a thermometer in 150 ml of water. A 10 min incubation was started when the thermometer reached 43° C., and then every 2 mins, the flasks were given a gentle mix by swirling the medium and cells within the flask. This was determined to be the optimal heat-shock conditions for Sf9 cells expressing pestivirus recombinant proteins. The cell culture flasks were then placed back into the incubator (at 28° C.), with shaking at 110 rpm, for a further 2-hr period to allow the insect-cell, heat-shock proteins (hsps) to be expressed and coupled to the pestivirus NS3 recombinant protein.

TABLE 8

| Recombinant Baculovirus | EMAI Virus number | Stock | Titre (pfu/ml) | Multiplicity of Infection |
|---|---|---|---|---|
| AcMNPV + Trangie E1/E2 | Z044 | Master | $2.8 \times 10^7$ | 1.0 |
| AcMNPV + Bega E1/E2 | Z376 | Seed | $1.0 \times 10^7$ | 1.0 |
| AcMNPV + Clover lane E1/E2 | Z361 | Working | $4.35 \times 10^7$ | 2.0 |
| AcMNPV + Bega E0 | Z341 | Master | $3.2 \times 10^6$ | 0.2 |

TABLE 8-continued

| Recombinant Baculovirus | EMAI Virus number | Stock | Titre (pfu/ml) | Multiplicity of Infection |
|---|---|---|---|---|
| AcMNPV + Trangie E0 | Z293 | Seed | $2.2 \times 10^7$ | 1.0 |
| AcMNPV + Trangie NS3/NS4A | Z346 | Master | $2.0 \times 10^6$ | 0.2 |

Heat Shock Conditions for E1/E2 and E0 Recombinant Baculovirus-Infected Cultures Sf9 insect cells infected with recombinant baculoviruses expressing either E1/E2 or E0 pestivirus proteins were incubated at 28° C., with shaking at 110 rpm, for a period of 24 hr. The infected cell cultures were then heat shocked exactly as described above (10 min at 43° C.). The cell cultures in their flasks were then returned to the incubator (28° C.) and the cells cultured, with shaking at 110 rpm, for a further period of 24 hr. In this system, the cultures expressing the E1/E2 proteins were heat shocked at 24 hr, as opposed to 48 hr for the NS3/NS4A protein, to ensure that the E1/E2 recombinant proteins were coupled to insect cell hsps prior to their transport out of the Sf9 cells and into the cell culture medium. Since it had not yet been determined whether the recombinant E0 pestivirus proteins were secreted from insect cells, or remained within the cells themselves, Sf9 cultures producing the E0 pestivirus proteins were also heat shocked at 24 hr after infection with the recombinant baculoviruses.

Heat Shock Conditions for Uninfected, Control-Cell Cultures

Uninfected Sf9 insect cell cultures were incubated at 28° C. (shaking at 110 rpm) for a period of 48 hr. These control cell cultures were heat shocked exactly as described above. The cell culture flasks were then returned to 28° C. in the incubator, with shaking at 110 rpm, for a further 2 hr incubation period to allow the insect cell heat shock proteins to be formed by the stressed cells.

Harvesting of Individual Recombinant Pestivirus Proteins from Sf9 Cell Cultures [NS3 Recombinant Protein+Heat-Shock Proteins (hsps)]

Cells were separated from the medium by centrifugation at 2000×g for 10 mins. The cell pellet, containing the NS3/NS4A antigen, was then resuspended in one sixth of the original volume using serum-free medium (Sf-900 II SFM; Gibco BRL) containing leupeptin (protease inhibitor, ICN Biomedicals, Inc) at a concentration of 5 μg/ml. This gave an effective six-fold concentration of the cells plus recombinant NS3/NS4A antigen. The cells were then freeze/thawed twice at −80° C. to break down cellular membranes and release the NS3 recombinant protein, together with recombinant baculovirus, into the medium.

Harvesting of Individual Recombinant Pestivirus Proteins from Sf9 Cell Cultures [E1/E2 Recombinant Protein+Heat-Shock Proteins (hsps)]

Cells were removed from the medium by centrifugation at 2000×g for 10 mins. Leupeptin (protease inhibitor) was again added to the supernatant, containing the expressed E1/E2 protein, to give a final concentration of 5 g/ml. The addition of the protease inhibitor prevented degradation of the expressed proteins.

Harvesting of Individual Recombinant Pestivirus Proteins from Sf9 Cell Cultures [E0 Recombinant Protein+Heat-Shock Proteins (hsps)]

In the case of insect-cell cultures expressing this particular protein, the whole culture (cells plus medium) was harvested and leupeptin added to give a final concentration of 5 µg/ml. The culture was then freeze/thawed twice to break down cellular membranes, releasing both the recombinant baculoviruses and any cell-associated E0 proteins into the medium.

Harvesting of Individual Recombinant Pestivirus Proteins from Sf9 Cell Cultures [Control Cells+Heat-Shock Proteins (hsps)]

Control (uninfected) cultures were harvested as described above for NS3/NS4A However, the control cells were concentrated 10-fold.

Beta-Propiolactone (βPL) Inactivation of Recombinant Baculoviruses

βPL inactivation (using β-propiolactone, Sigma Aldrich Fine Chemicals) was carried out twice on all recombinant protein preparations produced by the baculovirus-vector expression-vector system, and for the control-cell preparation. The standard method employed by the Commonwealth Serum Laboratories (CSL, "Inactivation of Baculovirus using Beta-Propiolactone, 1998") was used in all cases. To ensure no residual infectious baculovirus was left in the "inactivated" material, each preparation was passaged three times in Sf9 monolayers. The final pass was titrated in an Sf9 plaque assay, using 1.5% carboxymethylcellulose (CMC, BDH; 6% CMC in deionised water diluted, 1 in 4 with complete TC100) containing 125 mg/ml X-gal (Boehringer Mannheim) as the overlay. Plaque assays were set up according the Invitrogen MaxBac Baculovirus Expression System Manual, Version 1.8, and the plaque assay read on day 7. There was no evidence of live, infectious baculovirus present in any of the preparations used to formulate the subunit vaccine, thus meeting the Australian Quarantine Inspection Service (AQIS) requirements for the use of the experimental vaccine in food-producing animals.

Concentration of the Recombinant E0 and E1/E2 Protein Preparations.

The Sf9 cells expressing the E0 recombinant proteins were separated from the medium after inactivation (as above) by centrifugation at 2000×g for 10 min and these cells were then stored at 4° C. pending their use. The supernatants containing recombinant E0 proteins were then concentrated five times in separate Amicon Ultrafiltration Cell steps, according to the manufacturer's instructions. The concentrated E0 protein-containing supernatant was then re-mixed with the E0 Sf9 cells to prepare the final, concentrated preparation.

In the case of the inactivated E1/E2 recombinant proteins, the supernatant fractions only were concentrated using the Amicon Ultrafiltration Cell. These proteins are all secreted from the recombinant-baculovirus infected cells and therefore the cell fraction is discarded.

Determination of the Amount of Recombinant Pestivirus Protein in each Preparation by Titration in the Pestivirus Antigen Capture ELISA (PACE).

The amount of recombinant protein, after βPL inactivation, was assayed by titrating each individual recombinant protein preparation in the modified PACE (see Shannon et al., 1991). The modification of the published method involved sample (50 µl/well) being added directly to a blocked, washed ELISA plate, and the plate incubated for 1 hr at 37° C. Antibody solution (50 µl/well) was then added. The antibody used was either biotinylated goat anti-pestivirus antiserum (pAb) or individual anti-E2 or anti-NS3 monoclonal antibodies (mAbs). The plate was incubated overnight at 22° C., then developed as described in Shannon et al. (1991), omitting the incubation with biotinylated anti-mouse IgG for samples that were reacted with the biotinylated goat antiserum.

It should be noted that recombinant E0 protein is not able to be detected in this assay system since the protein failed to react with either of the polyclonal or monoclonal antibodies. Therefore, it was assumed that this protein was similar in concentration to those determined for the analogous E1/E2 expressed structural glycoproteins.

Summary of the Recombinant Proteins Incorporated in the Subunit Vaccine

The recombinant pestivirus proteins Trangie NS3/NS4A, Trangie E0, Bega E0, Trangie E1/E2, Bega E1/E2, Clover Lane E1/E2, together with the Control cells, were prepared by the methods described in this example. However, Bega and Trangie E1/E2 were not heat shocked, Trangie E1/E2 was concentrated six times instead of five and the BDV Clover Lane E1/E2 recombinant protein was processed as described for the recombinant E0 protein preparations.

Recombinant, Experimental Subunit Vaccine

The composition of the vaccine preparations used in Example 4 are set out in Table 9. In summary, each dose of the recombinant pestivirus vaccine contained: 1 ml Bega E0, 1 ml of Trangie E0, 1 ml of Clover Lane E1/E2, 0.5 ml Trangie E1/E2, 1 ml of Bega E1/E2 and 0.3 ml of Trangie NS3/NS4A. Thimerosal (mercuric compound, Sigma Aldrich) was added to the vaccine mixture to help prevent bacterial contamination, with a final concentration in the vaccine of 0.1% (w/v). Isocomatrix adjuvant (Commonwealth Serum Laboratories, Australia) was used at the rate of 2 mg incorporated in each vaccine dose. The formulated vaccine was stored at 4° C. until injected into the cattle (initial dose followed by a sec dose 4 weeks later).

Control Vaccine

The formulation of the Control vaccine is also set out in Table 9. In summary, each dose of control vaccine contained 4.8 ml of the control-cell preparation. Thimerosal was again added to the control vaccine to help prevent bacterial contamination, the final concentration in the vaccine being 0.1% (w/v). Isocomatrix adjuvant (CSL) was incorporated at 2 mg per vaccine dose, in line with the rate used in the experimental vaccine. The control vaccine preparation was stored at 4° C. until required. Two doses were given to the control animals in the trial on the same days as the experimental subunit vaccine was administered to the vaccinated animals.

TABLE 9

Summary of Subunit, expressed - protein Vaccine preparation

| | |
|---|---|
| Trangie NS3/NS4A | Labelled: TNS3 Apr. 8, 1998 |
| | MOI 0.2, grown for 48 hrs in SFM |
| | Heat shocked at 43° C. for 10 mins |
| | Placed back in incubator for 2 hrs with shaking |
| | ONLY cells harvested (S/N discarded), therefore [ ] 6× |
| | Leupeptin added to give 5 ug/ml |
| | Freeze/thawed 2 times |
| | BPL inactivated 2 times using CSL standard method |
| | Stored at −80° C (Block 5) |
| Trangie E0 | Labelled: TEO Apr. 23, 1998 |
| | MOI 1, grown for 48 hrs in SFM |
| | Heat shocked at 43° C. for 10 mins |
| | Placed back in incubator for 24 hrs with shaking |
| | Cells + S/N harvested |

TABLE 9-continued

Summary of Subunit, expressed - protein Vaccine preparation

| | |
|---|---|
| Bega E0 | Leupeptin added to give 5 ug/ml<br>Freeze/thawed 2×<br>BPL inactivated 2 times using<br>CSL standard method<br>AMICON concn. 5×<br>Stored at −80° C. (block 5)<br>Labelled: BE0 Apr. 23, 1998<br>MOI 0.2, grown for 48 hrs in SFM<br>Heat shocked at 43° C. for 10 mins<br>Placed back in incubator for 24 hrs<br>with shaking<br>Cells + S/N harvested<br>Leupeptin added to give 5 ug/ml<br>Freeze/thawed 2×<br>BPL inactivated 2 times using<br>CSL standard method<br>AMICON concn 5×<br>Stored at −80° C. (Block 5) |
| Clover Lane E1/E2 | Labelled: CLE2 Apr. 23, 1998<br>MOI 2, grown for 48 hrs in SFM<br>Heat shocked at 43° C. for 10 mins<br>Placed back in incubator for 24 hrs<br>with shaking<br>Cells + S/N harvested<br>Leupeptin added to give 5 ug/ml<br>Freeze/thawed 2 times<br>BPL inactivated 2 times using<br>CSL standard method<br>AMICON concn. 5×<br>Stored at −80° C. (Block 5) |
| Trangie E1/E2 | Labelled: TE2 May 8, 1998<br>MOI 1, grown for 48 hrs in SFM<br>ONLY S/N harvested<br>Leupeptin added to give 5 ug/ml<br>Freeze/thawed 2 times<br>BPL inactivated 2 times using<br>CSL's standard method<br>AMICON concn. 6×<br>Stored at −80° C. (Block 5) |
| Bega E1/E2 | Labelled: BE2 May 8, 1998<br>MOI 1, grown for 48 hrs in SFM<br>ONLY S/N harvested<br>Leupeptin added to give 5 ug/ml<br>Freeze/thawed 2 times<br>BPL inactivated 2 times using<br>CSL standard method<br>AMICON concn. 5×<br>Stored at −80° C. (Block 5) |
| Control Vaccine | Labelled: SFM-Sf9 Jun. 24, 1998<br>Grown for 48 hrs in SFM<br>Heat shocked at 43° C. for 10 mins<br>Placed back in incubator for 24 hrs<br>with shaking<br>Cells harvested and taken up in<br>50 ml SFM therefore [ ]10×<br>Leupeptin added to give 5 ug/ml<br>Freeze/thawed 2 times<br>BPL inactivated once using CSL<br>standard method<br>Stored at −80° C. (Block 5) |

Mixing of recombinant proteins to produce the subunit vaccine

| Rec Antigen | 1 × DOSE | 27 × DOSES |
|---|---|---|
| BE0 | 1 ml | 27 ml |
| TE0 | 1 ml | 27 ml |
| CLE1/E2 | 1 ml | 27 ml |
| TE1/E2 | 0.5 ml | 13.5 ml |
| TNS3/NS4A | 0.3 ml | 8.1 ml |
| BE1/E2 | 1 ml | 27 ml |
| Total Volume | | 129.6 ml |

Added 1.29 ml Thimerosal to 129.6 ml vaccine mix, took out 9.6 ml and placed into 1 ml aliquots for storage at −20° C. (freezer in Block 5 egg room).
To the remaining 120 ml, added 32.5 ml Iscomatrix adjuvant and stirred for 2 mins to mix well.
Aliquoted into 2 containers i.e 68 ml/container and stored at 4° C.
Set up vaccine in 10 ml syringes with 18 gauge needles - 6 ml/dose final volume.

Control vaccine

| | 1 dose | 6 doses |
|---|---|---|
| Control cell preparation | 4.8 ml | 28.8 ml |
| Iscomatrix adjuvant | 1.3 ml | 7.8 ml |
| Thimerosal | 0.048 ml | 0.29 ml |

The control vaccine was set up in 10 ml syringes with 18 gauge needles - 6 ml/dose final volume

EXAMPLE 3

The Effect of the Subunit Vaccine on Australian Cattle Format of the Subunit Foetal Protection Trial A total of 22 pestivirus antibody negative, non-pregnant heifers were selected for the trial. A group of animals (n=10) were vaccinated twice, 4 weeks apart, with the subunit protein vaccine (6 ml) as prepared in examples 1 and 2. A further group of animals (n=12) were vaccinated with the control preparation (6 ml). All animals were bled at regular intervals and the concentrations of both anti-E2 and anti-NS3 antibodies were determined using the complex-trapping-blocking ELISA (CTB-ELISA) format as carried out by the Elizabeth Macarthur Agricultural Institute (EMAI).

Immediately after the second vaccination, the animals were synchronised for oestrus. Insemination occurred immediately after oestrus was detected. All animals were judged to have become pregnant and have developing foetuses of greater than 6 weeks of age, at 11 weeks after the second vaccination, a time considered to be the most susceptible for infection with the challenged BVDV isolate. The heifers were then challenged with a dose ($3 \times 10^6$ $TCID_{50}$) of the live heterologous BVDV isolate Glen Innes.

Six weeks following viral challenge, all heifers were slaughtered at an export abattoir (Mudgee) in the two groups. The foetuses were collected from pregnant heifers. That is, there were 7 foetuses from the 10 animals in the vaccinated group and there were 9 foetuses from the 12 animals in the control group.

Individual foetal tissues were collected under sterile conditions. Several methods were employed to test for the presence of BVDV infection. Firstly, two antigen-capture ELISAs specific for either E2 antigens or NS3 antigens were used. Secondly, a panel of monoclonal antibodies was used to detect infected cells isolated using standard techniques and immunoperoxidase (IPX) staining. Thirdly, a 5'-UTR virus-specific RT-PCR was used. The combination of these methods gave a sensitive and specific detection of infected versus non-infected foetuses collected from the heifers.

Effect of E2 Subunit Vaccine on Cattle Immune Response to BVDV

The average concentration of anti-E2 (neutralising) antibody in both the vaccinated and control groups of heifers, before and after vaccination, and after live virus challenge, is shown in FIG. 1.

The average concentration of anti-E2 antibody plotted over time indicated that the subunit vaccine resulted in very high concentrations of anti-E2 antibody in the vaccinated group. High titers of antibody commenced as early as 2 weeks after the administration of the second dose of vaccine. The concentration of anti-E2 antibody in vaccinated heifers was significantly higher than in the control group. The concentration of anti-E2 in the vaccinated group declined slightly over the preceding 9 weeks, but still remained significantly higher than the control group of heifers.

A rapid anamnestic rise in the concentration of E2 antibody in the vaccinated group was observed at 7 days post challenge with the live BVD virus, which continued to rise until 9 days post challenge, where it remained at a sustainable maximum concentration. In contrast to this trend, an increase in the concentration of anti-E2 antibody was only observed in the control group after challenge with the live virus. The onset of a normal response in the control group was then observed, with the average concentration of anti-E2 antibody beginning to develop at 14 days post challenge. However, a maximum response was not reached until 3 to 4 weeks post challenge.

Thus the vaccination of pregnant heifers with the subunit vaccine creates an immune response in the heifer during the first 4 to 7 days after viral infection. This is an important stage during which the live virus crosses the placenta to the developing fetus. These results clearly indicate that the replication of the live virus was antagonised in the subunit vaccinated group of heifers (n=10). This is the first time that such a response has been reported for a subunit vaccine.

Effect of NS3 Subunit Vaccine on Cattle Immune Response to BVDV

The concentration of anti-NS3 antibody in both vaccinated and control groups of heifers over time is shown in FIG. 2. Surprisingly, there was no anti-NS3 antibody detected in the vaccinated heifers after vaccination. The reason for this is not yet known. However, this result has a great potential for the development of a "marker" vaccine. All "naturally infected" animals develop anti-NS3 antibodies 21 days after infection with BVDV. Since animals vaccinated with the subunit vaccine do not develop anti-NS3 antibodies (discussed below), they are easily distinguishable from "naturally infected" animals.

It is likely that anti-NS3 protein results in the generation of a strong cell-mediated immune response through the induction of CD8+ cytotoxic T cells although failing to elicit an antibody response.

After challenge with the live virus, vaccinated heifers (7 out of 10) showed no significant development of anti-NS3 antibodies until 5 to 6 weeks post challenge. The remaining three vaccinated heifers developed anti-NS3 antibodies 3 to 6 weeks post challenge. However, the concentration of antibodies was significantly lower than the control group of heifers. In contrast, the control heifers (n=12) developed a normal antibody response commencing 14 to 18 days post challenge, reaching a peak 4 weeks post challenge (FIG. 2).

These results clearly indicate that the replication of the live virus was inhibited in the subunit vaccinated group of heifers (n=10). This is the first time that such a response has been reported for a subunit vaccine. It is evident that the postulated early onset of CTL responses directed against infected cells prevented the replication of the virus. Thus there was insufficient virus circulating in the vaccinated animals to cross the placenta and infect the fetus.

The Concentration of Neutralising Antibodies Induced by the Subunit Vaccine

Serum neutralisation tests (SNTs) were carried out using different BVDV isolates to investigate the concentration of neutralising antibodies induced by the subunit vaccine, and to determine the anamnestic responses resulting from live virus challenge.

The results of this experiment are shown in Table 10. As expected from the results shown in FIG. 1, no antibody response was observed prior to vaccination in the vaccinated group of heifers. However, after the second vaccination, a very good anti-E2 neutralising antibody response (average titre of 1 in 1000) was observed in the 2 BVDV isolates associated with the vaccine (Trangie and Bega). In contrast, there was a very low response of neutralising antibody (average titre of 1 in 50) against the sheep BDV isolate (Clover Lane) even though the recombinant E2 protein from this virus was incorporated in the vaccine in combination with hsps. However, the resulting concentration of neutralising antibody was greater from this subunit vaccine than that achieved with the use of inactivated whole Clover Lane virus in a previous experiment (results not shown).

SNTs conducted on the heterologous challenge virus Glen Innes indicated a surprisingly high cross-reactivity (average titre 1 in 1200) at 4 weeks after the second dose of vaccine. This finding confirms that the combination of E2 proteins results in good cross protection against heterologous viruses. An even more distant BVD virus Braidwood showed a lower concentration of neutralising antibodies (average titre of 1 in 400) but does correspond with a significant antibody production against infection with this virus.

The SNT assays carried out on serum collected from the vaccinated animals at 7 and 14 days post challenge (Table 10) were even more surprising. Assays were conducted using each of the 3 viruses represented in the subunit vaccine. It is evident from the results that there was an extremely high anamnestic response in the anti-E2 antibody levels at just 7 days post challenge. Average SNT for both Trangie and Bega BVDV viruses were in the order of 1 in 14 000 to 16 000 at 7 days but rose to an extraordinary concentration by day 14 post challenge. At 14 days post challenge, the average titre against Trangie was 1 in 180 000, with 2 animals having titres as high as 1 in 512 000. Similarly, titres against Bega were on average 1 in 100 000 at 14 days, with 3 animals having titres against Bega of 1 in 256 000. The magnitude of these titres is rarely seen in "naturally infected" animals.

TABLE 10

| Vaccinated Animal Number | SNT at 4 weeks post second vaccination with subunit vaccine+ | | | | SNT at 7 days post challenge with Glen Innes virus+ | | | SNT at 14 days post challenge with Glen Innes virus♦ | | |
|---|---|---|---|---|---|---|---|---|---|---|
| | Trangie | Bega | Clover Lane | Glen Innes | Braidwood | Trangie | Bega | Clover Lane | Trangie | Bega | Clover Lane |
| Q239 | >2056 | >2056 | 32 | >2056 | 1024 | 12800 | 12800 | 800 | 12800 | 64000 | 8000 |
| Q269 | 512 | 128 | 16 | 256 | 64 | 3200 | 3200 | ~4 | 16000 | 16000 | 64 |
| Q300 | 256 | 512 | 128 | 512 | 128 | 6400 | 12800 | 800 | 64000 | 32000 | 8000 |
| Q306 | 1028 | 256 | 16 | 1028 | 256 | 12800 | 51200 | 1600 | 64000 | 64000 | 4000 |
| Q324 | 1028 | 512 | 128 | 1028 | 256 | 3200 | 1600 | 400 | 64000 | 16000 | 4000 |
| Q354 | 128 | 64 | <4 | 128 | 16 | 3200 | 1600 | 100 | 64000 | 64000 | 2000 |
| Q355 | 1028 | >2056 | 32 | 2056 | 512 | 12800 | 12800 | 1600 | 512000 | 256000 | 16000 |
| Q379 | 2056 | >2056 | 32 | >2056 | 1024 | 25600 | 12800 | 1600 | 128000 | 64000 | 8000 |
| Q382 | 512 | 512 | 64 | >2056 | 64 | 6400 | 6400 | 100 | 256000 | 256000 | 8000 |
| R346 | >2056 | >2056 | 64 | >2056 | 1024 | 51200 | 51200 | 3200 | 512000 | 256000 | 64000 |
| Mean Titre | 1028 | 1020 | 50 | 1200 | 436 | 13700 | 16600 | 1024 | 18000 | 108000 | 12250 |
| (Range) | (128–2056) | (64–>2056) | (0–128) | (128–>2056) | (16–1024) | (3200–51200) | (1600–51200) | (~4–3200) | (16000–512000) | (16000–256000) | (64–64000) |

♦ = scrum dilutions started at 1 in 4; 2-fold dilutions to end-point;
+ = scrum dilutions started at 1 in 1000 for Trangie and Bega, 1 in 100 for Clover Lane; 2-fold dilutions to end-point.

TABLE 11

| | Reciprocal of SNT (NPLA) Titre (4 weeks after second vaccination in both trials) | | | | | |
|---|---|---|---|---|---|---|
| Vaccinated Animal Number | Inactivated Vaccine 1112/96 (T + B + CL) | | | Subunit Vaccine 584/98 (T + B + CL) | | |
| | Trangie⊕ | Glen Innes∴ | Clover Lane⊕ | Trangie⊕ | Glen Innes∴ | Clover Lane⊕ |
| 1 | 1024 | 512 | 10 | >2048 | >2048 | 32 |
| 2 | 256 | 512 | 20 | 512 | 256 | 16 |
| 3 | 256 | 512 | 20 | 256 | 512 | 128 |
| 4 | 40 | 64 | 10 | 1024 | 1024 | 16 |
| 5 | 50 | 50 | 10 | 1024 | 1024 | 128 |
| 6 | 200 | 256 | 8 | 128 | 256 | <4 (0) |
| 7 | — | — | — | 1024 | 2048 | 32 |
| 8 | — | — | — | 2048 | >2048 | 32 |
| 9 | — | — | — | 512 | >2048 | 64 |
| 10 | — | — | — | >2048 | >2048 | 64 |
| Mean Titre | 300 | 300 | 12 | 1028 | 1200 | 50 |
| (Range) | (40–1024) | (50–512) | (8–20) | (128–2048) | (128–>2048) | (0–128) |

Comparison of the neutralising titres against 3 viruses measured in cattle at 4 weeks after vaccination with either the inactivated, whole-virus vaccine or the non-infectious, subunit vaccine containing recombinant proteins.
⊕Trangie (BVDV isolate) and Clover Lane (BDV isolate) incorporated in both vaccines. In subunit vaccine, Clover Lane E2 recombinant protein was coupled in vivo with heat shock proteins (hsps);
∴ = Glenn Innes was the challenge live virus used in both trials (a BVDV isolate clearly distinct from the vaccine viruses).

Thus it can be concluded that the subunit vaccine had a significant effect in "priming" animals for a reaction against live virus challenge that has not previously been observed.

The SNT assays indicated a strong "priming" response against the BDV isolate Clover Lane (Table 10). At 7 days post challenge with a totally unrelated live virus (BVDV Glen Innes) the SNTs against Clover Lane indicated a titre of 1 in 1024 (increased from 1 in 50 observed following vaccination). The titre against Clover Lane rose at 14 days to an average of 1 in 12 000, with one animal giving a titre of 1 in 64 0000 against the sheep isolate. This provides further evidence that the subunit vaccine provides wide spread protection against all Australian cattle and sheep pestiviruses. This protection is far greater than presently available with inactivated whole virus vaccines.

Additional SNTs were carried out against 3 Australian pestiviruses. Two groups of animals were vaccinated with two different vaccines derived from the Trangie+Bega+Clover Lane isolates and were thus directly comparable. In the first group, animals were vaccinated with an experimental inactivated whole virus vaccine. The second group of animals was vaccinated with the subunit vaccine (+hsps). Serum was collected from the vaccinated cattle in both groups 4 weeks after 2 doses of the vaccine.

The results for the SNTs against the 3 viruses are shown in Table 11. A comparison of all 3 viruses showed that the subunit vaccine resulted in titres at least 4 times higher than the corresponding titres induced by the inactivated vaccine. In addition, cross neutralisation occurred for both vaccines against the totally unrelated BVDV isolate "Braidwood", which showed a similar 4 fold increase in the titre at 4 weeks post vaccination with the subunit vaccine when compared to the inactivated vaccine (results not shown).

Thus the requirement for a wider ranging vaccine in all cattle-producing countries is met by the development of this subunit vaccine.

Effect of Subunit Vaccines on Transfer of BVDV to the Fetus

Tissue samples collected from foetuses (n=7) obtained from the pregnant vaccinated heifers and from foetuses (n=9) obtained from the pregnant control heifers were tested at EMAI using 3 different BVDV-specific assays (Table 12) as described previously. It was apparent from all 3 tests that there was no BVDV infections in any of the 7 foetuses obtained from the pregnant vaccinated heifers. In contrast, 5 of the 9 foetuses in the control group were infected as shown by the virus isolation and RT-PCR assays.

Therefore, it was concluded that vaccination gave 100% protection against a live, heterologous BVDV challenge at a time when there is a maximum chance of transferring virus into the developing foetus.

TABLE 12

| Foetus harvested from Animal No. | Antigen ELISA (PACE) Results (S/N Ratios)* | | | | 5' UTR RT-PCR Results | |
|---|---|---|---|---|---|---|
| | E2[Δ] | NS3 | E2 + NS3 | Final Result | VI 2nd Pass | RT-PCR (+/−) |
| Vaccinates | | | | | | |
| Q239 | 1.0 | 1.1 | −ve | −ve | −ve | −ve |
| Q306 | 1.0 | 0.9 | −ve | −ve | −ve | −ve |
| Q324 | 1.0 | 1.2 | −ve | −ve | −ve | −ve |
| Q354 | 1.0 | 1.1 | −ve | −ve | −ve | −ve |
| Q355 | 0.9 | 1.0 | −ve | −ve | −ve | −ve |
| Q379 | 1.2 | 1.1 | −ve | −ve | −ve | −ve |
| R346 | 1.0 | 0.9 | −ve | −ve | −ve | −ve |
| Controls | | | | | | |
| Q240 | 1.2 | 1.1 | 1.0 | −ve | −ve | −ve |
| Q316[Φ] | 0.7 | 0.6 | <1.0 | −ve | +ve[ſ] | +ve |
| Q352 | 1.0 | 1.0 | 1.0 | −ve | −ve | −ve |
| Q373 | 0.9 | 1.1 | 1.0 | −ve | −ve | −ve |
| Q388 | 2.9 | 13.6 | 15.8 | +ve | +ve | +ve |
| R298 | 4.9 | 10.8 | 11.1 | +ve | +ve | +ve |
| Q337 | 1.0 | 0.9 | 1.0 | −ve | −ve | −ve |
| Q372 | 3.2 | 12.8 | 14.1 | +ve | +ve | +ve |
| Q385 | 2.3 | 16.2 | 17.6 | +ve | +ve | +ve |

*= signal-to-noise ratios. Ratio >2.0 are positive in PACE on foetal tissues.
[Δ]= Positive E2 results low. Results confirmed by high S/N ratios with NS3 monoclonals on positive tissues.
[Φ]= foetus was clearly dead in utero. Results confirmed foetus was infected.
[ſ]Weak virus isolation positive-only individual cells strained on microplate. Virus titre therefore low in this dead fetus. Results confirmed by diagnostic RT-PCR

EXAMPLE 4

The Effect of the Subunit Vaccine on Australian Sheep

Two additional trials on subunit proteins were conducted in sheep to investigate further the protective effect of these vaccines. These trials were conducted to examine the effect of a combination of proteins (coupled with heat-shock proteins) compared to a single viral protein with/without heat shock proteins in affording foetal protection against the transfer of the same live, heterologous pestivirus used in the cattle trial. Although the same BVDV isolate ('Glen Innes') was used for challenge in the sheep, the dose was reduced to $2 \times 10^5$ TCID$_{50}$ per sheep, or 50 times less live virus than was used for challenge in cattle.

In the first of these trials involving 24 sheep, the same cattle subunit vaccine was prepared using two different commercial adjuvant preparations. Two groups of 8 sheep were each given 2 doses of subunit proteins while 8 sheep were injected with a control preparation containing insect cells, but no pestivirus proteins. Antibody assays for anti-E2 and anti-NS3 antibodies in the serum of vaccinated and control sheep over the course of the study were carried out in the same way as for the cattle subunit trial. A ram was put in with the ewes immediately after the second vaccination. At 10 weeks after vaccination, when all of the ewes were pregnant, they were challenged with live, heterologous pestivirus (Glen Innes virus). Five weeks later, all of the ewes were slaughtered and the foetuses collected for assays to establish whether they showed pestivirus infection in the foetal tissues. The absence of any detectable pestiviruses in the foetal tissues showed that there had been no transfer of virus from the ewe to her foetus. This equated with complete protection and was measured only in the two vaccinated groups of animals (see below).

The antibody responses in the vaccinated and control groups of sheep in are presented in FIGS. 3 and 4. It can be seen that the vaccinated animals responded by producing high levels of anti-E2 antibody (equivalent to neutralising antibody), beginning 2 weeks after the second dose of vaccine. This was a similar response to the anti-E2 antibody response in cattle vaccinated with the same subunit vaccine. However, it is noteworthy that the absolute levels of anti-E2 antibody measured by ELISA in the vaccinated sheep (FIG. 3) were less than the comparable levels measured in vaccinated cattle. Like cattle, there was an immediate, anamnestic response in the vaccinated sheep with high levels of anti-E2 antibody measured at just 7 days after challenge with the live virus. This is good evidence that the subunit-vaccinated sheep produced early, protective, antibody responses, just as vaccinated cattle showed in Example 3.

As in cattle, sheep did not produce any anti-NS3 antibody following vaccination (FIG. 4) confirming that the subunit preparation is a 'marker vaccine'. Following live-virus challenge of the vaccinated sheep, it is highly significant that 14 of the 16 sheep had not produced any anti-NS3 antibody by 5 weeks after challenge, when the ewes were slaughtered. The remaining 2 sheep had produced only moderate anti-NS3 antibody levels, when compared to the levels of anti-NS3 antibody in the control, unprotected sheep at the same time point (see FIG. 4). Taken together, these results are clear evidence that subunit vaccination in the sheep reduced viral replication in the ewes after challenge with the live BVD virus. Thus, the anti-NS3 antibody results in sheep confirm and extend the results seen in subunit-vaccinated cattle. It was therefore of importance to see if the reduced viral replication in the sheep equated with protection from transfer of virus into the foetuses of the vaccinated ewes.

The foetal assay results showed that there was no difference in the foetal protective index between the 2 vaccinated groups. There was therefore no effect of changing the adjuvant used in the 2 formulations of vaccine. The results from both groups were able to be pooled, giving 16 foetuses from the vaccinated ewes for comparison with 8 foetuses from the control, unprotected ewes. Analyses of all results showed that, overall, there was 56% complete foetal protection (9/16 foetuses protected) in the vaccinated ewes compared to 100% infection rate (8/8 foetuses infected) in the control ewes. However, the rate of transfer of live pestivirus into 5/7 of the positive foetuses collected from the vaccinated ewes was dramatically reduced compared to the foetuses from the control ewes (Table 13). This meant that only 2/16 foetuses in the vaccinated ewes contained similar amounts of virus to the levels in the control-group foetuses. Thus, in 87% of the vaccinated ewes, there was either no transfer of virus, or a severely-restricted transfer.

This shows that the subunit vaccine, although not as effective in sheep as it is in cattle, still gives a high level of protection in vaccinated ewes. Both trials showed significant, strong protective results for the subunit vaccine preparation. As discussed below, the difference in results between cattle and sheep is likely to be the result of less resistance in sheep to the effects of a cattle-pestivirus challenge. This represents an inter-species transfer of virus and sheep may have less effective methods of protection from a virus that has crossed the species barrier.

TABLE 13

Amount of virus (50% Tissue-Culture Infectious Dose - $TCID_{50}$) in foetal tissues collected from subunit-vaccinated and control (unprotected) ewes

| Foetus No. | $Log_{10}$ Pestivirus $TCID_{50}$ per gram in Foetal Tissues | |
|---|---|---|
| | Vaccinated ewes | Control (Unprotected) Ewes |
| Number positive | 7/16 = 44% | 8/8 = 100% |
| 1 | <2.3 | 6.7 |
| 2 | <2.3 | 5.9 |
| 3 | 4.9 | 7.0 |
| 4 | 3.0 | 6.3 |
| 5 | 3.0 | 7.4 |
| 6 | 5.4 | 6.8 |
| 7 | 2.5 | 3.4 |
| 8 | Remaining 9 foetuses (56%) = Novirus | 6.7 |
| Mean ($Log_{10}$) ± SD | 3.34±1.2□□(7) | 6.2 ± 1.2 (8) |

□□Statistically significant decrease in viral amount in tissues ($P < 0.01$)
Notes:
Almost 1000 times less virus in the 7 foetuses from vaccinated ewes compared to the average level in 8 foetuses from unprotected ewes.
14 of the 16 foetuses in subunit-vaccinated ewes either fully protected (9) or with <$10^3$ virus particles per gram of tissue (5 foetuses). Therefore, complete or partial protection from foetal transfer of virus in vaccinated ewes = 87%.

A second trial conducted in 24 sheep investigated the protective effect of just one immunogenic protein from cattle pestiviruses. A total of 16 sheep, in 2 groups of 8, were vaccinated with 2 different preparations of the pestivirus envelope glycoprotein, E2, either coupled to heat-shock proteins (hsps) or with no hsps present. A further 8 sheep were injected with a control preparation that contained neither pestivirus protein, nor hsps. The trial format was the same as in the previous trial and the foetal assay results showed that a single pestivirus subunit glycoprotein incorporated in a vaccine gave only weak protection against the transfer of the same live BVD virus (Glen Innes) into the foetus. Overall, there was only 29% protection in the vaccinated ewes with the other 71% of foetuses infected. However, it is noteworthy that the vaccine where the E2 glycoprotein was associated with hsps gave almost twice the protective effect as the vaccine where there were no hsps. While the result was not significant due to the low numbers of protected foetuses involved, the trend shows that hsps do have an effect in enhancing vaccine efficacy. There was, again, a 100% infection rate (7/7) in the control ewes. This trial clearly demonstrated that more than one protein from pestiviruses is required to give high levels of protection. It is clear from both the cattle and sheep trials that a critical component of the subunit vaccine is the non-structural protein NS3/NS4A coupled to heat-shock proteins. The role of the smaller envelope glycoprotein E0 is less clear but has a probable role in protection as well.

EXAMPLE 5

Multiple-Expression Systems for Pestivirus Proteins

To improve the commercial viability of subunit pestivirus vaccines it is necessary to express more than one protein in a recombinant baculovirus. This cuts down the time-consuming and expensive culture systems inherent in single-protein expression. In order to achieve the goal of reducing 6 different expression systems involved in the original subunit preparation to a maximum of 2 cultures we investigated the possibility of genetically-engineering baculovirus multiple expression-vectors.

The commercial Multiple Transfer Plasmid, pBAC4x-1, was purchased from Novagen (Catalogue no. 70045-3) and 4 different genomic regions of two BVD viruses were successfully inserted into this plasmid. The E1/E2 regions from the Australian viruses Trangie and Bega, together with the truncated NS3 region from the Trangie virus and a capsid/E0 region from the same virus, were inserted in the 4 multiple-restriction sites of the plasmid in the following order such that TC/E0 and BE1/E2 were under the control of the baculovirus p10 promoter and TE1/E2 and TNS3/NS4A were under the control of the baculovirus polyhedrin promoter. All 4 genomic regions were subsequently shown to be in the correct orientation, giving a transfer plasmid that contained the correct genetic information for 4 different BVDV proteins.

Recombinant baculoviruses were then constructed by transfection using the pBAC4x-1 transfer plasmid before being cloned in a series of plaque assays. The recombinant baculoviruses generated were tested at each stage of the cloning process to see if they would express all 4 proteins at high levels in Sf9 insect-cell cultures. One recombinant virus was shown to have stable, high-level expression of all 4 proteins after 3 rounds of plaque purification followed by 3 passes of the cloned virus in Sf9 cultures. The levels of expression for each of the 4 proteins were assayed by titration using specific monoclonal antibodies. The results for protein levels in both supernatant and in cells are shown in Table 14. It can be seen that all 4 proteins were produced in a single-culture system at very high levels, with the individual titration end-points in the range of 1 in 64 to 1 in 4096.

TABLE 14

Multiple protein-expressing baculovirus cloned 3 times by limiting dilution and passed 3 times in Sf9 cells. Recombinant baculovirus stable and able to express all proteins to a high level.

| Antigen | Endpoint Dilution | Detecting Antibody |
|---|---|---|
| Trangie and Bega E2 (Supernatant) | 1 in 4096 | E2 mAb mix (R1465) |
| Trangie E0 (Supernatant) | 1 in 256 | E0 mAb 15c5 (R495) |
| Trangie NS3 (Supernatant) | 1 in 64 | NS3 mAb mix (R1526) |
| Trangie and Bega E2 (Cells) | 1 in 1024 | E2 mAb mix (R1465) |
| Trangie E0 (Cells) | 1 in 4096 | E0 mAb 15c5 (R495) |
| Trangie NS3 (Cells) | 1 in 256 | NS3 mAb mix (R1526) |

To further investigate whether the multiple-expression system would be suitable for vaccine production, the Sf9 cells infected with the recombinant 4x-protein was also subjected to heat shock (43° C. for 10 min). Protein production in the culture was followed and the final yields of protein suitable for incorporation in a vaccine ascertained at 4 days. A comparison was made with the levels produced in cultures not subjected to heat shock. The following Table (15) presents the results of assaying protein levels in a harvest of both supernatant and cells from each of the cultures:

TABLE 15

Titration endpoint levels for E2, E0 and NS3 proteins harvested from both supernatant and cells in the multiple-expression system. Cultures were grown at 27.5° C. for 4 days and one culture subjected to heat-shock to couple the pestivirus proteins to hsps. Comparative levels with/without hsps are shown.

| Expressed Pestivirus Protein | Titration endpoint No hsps | Titration endpoint With hsps coupled |
|---|---|---|
| E1/E2 (Trangie + Bega) | 1 in 1024 | 1 in 2048 |
| Capsid/E0 (Trangie) | 1 in 1024 | 1 in 2048 |
| Truncated NS3 (Trangie) | 1 in 1024 | 1 in 1024 |

It is noteworthy that protein production in the heat-shocked culture containing the multiple-protein expressing recombinant pestivirus was not affected by heat-shock treatment. Therefore, the baculovirus does not decrease protein production and high levels of proteins coupled to hsps are possible with this system. It is concluded that this system is eminently suitable for vaccine production purposes.

By way of a further example, a second Multiple Transfer Plasmid is constructed containing cDNA encoding further pestivirus proteins, namely Trangie E1/E2, Clover Lane E1/E2 and Clover Lane NS3/NS4A and optionally Clover Lane E2/Bega E0. It is considered that these additional proteins will extend the protective effect of subunit vaccines to cover a wider range of the antigenic diversity shown by BVDV isolates in the field. In particular, the inclusion of the 2 border disease virus (BDV) proteins from the 'Clover Lane' isolate will extend the protective effect to match that of the original subunit vaccine containing 6 proteins. In this way, just 2 cultures subjected to a short period of heat treatment will produce 6 different pestivirus proteins coupled to hsps. These can be tested in cattle for efficacy in protecting against the transfer of live pestivirus into the developing foetus, in the same way as described in Example 3.

REFERENCES

Abuchowski et al., 1981, supra;
Ausubel, et al. *Current protocols in molecular biology*
Becher P., Orlich, M. and Thiel, H.-J. (1998). Journal of Virology 72, 5165-5173.
Collett, M S, Anderson D K and Retzel E (1988). Journal of General Virology, 69, 2637-2643.
Current Protocols in Molecular Biology (1991): Supplement 15, K. Janssen (ed). Current Protocols, Wiley, p. 8.5.3.
Gibco BRL (1995): Guide to Baculovirus Expression Vector Systems (BEVS) and Insect Cell Culture Techniques.
Glover ed., *DNA Cloning: A Practical Approach*, Volumes I and II, MRL Press, Ltd., Oxford, U.K. (1985)
Heery D M. (1990). Trends in Genetics 6, 1.73.
Martin, *Remington's Pharmaceutical Sciences,* 18th Ed., Mack Publishing Co., Easton, Pa., (1990)
Newmark et al., *J. Appl. Biochem.,* 4:185-189 (1982).
Pauly T, Elbers K, Konig M, Lengsfeld T., Saalmuller A and Theil H J (1995). Journal of General Virology, 76, 3039-3049.
Sambrook, J., Fritsch, E. and Maniatis, T. (1989): Molecular Cloning: A Laboratory Manual. second ed. Cold Spring Harbor Laboratory Press, New York.
Shannon A D, Richards S G, Kirkland P D and Moyle A. (1991). Journal of Virological Methods 34, 1-12.
Smith et al (1983) *Mol Cell Biol* 12: 2156-2165

The invention claimed is:

1. A method of producing an immunogenic complex comprising a heat shock protein (hsp) coupled to a heterologous antigenic polypeptide, which method comprises:
   (a) expressing the antigenic polypeptide in a non-mammalian cell which cell has been subjected to a stimulus which causes the induction of a heat shock response in said cell; and
   (b) recovering the antigenic polypeptide coupled to one or more hsps from said cell or the culture medium.

2. The method according to claim 1 wherein the cell is a non-mammalian eukaryotic cell and the hsp is a non-mammalian eukaryotic hsp.

3. The method according to claim 2 wherein the cell is an insect cell and the hsp is an insect hsp.

4. The method according to claim 3 wherein the antigenic polypeptide is an antigen of a pathogenic organism.

5. The method according to claim 4 wherein the pathogenic organism is a virus or a bacterium.

6. The method according to claim 5 wherein the virus is a pestivirus.

7. The method according to claim 6 wherein the virus is bovine viral diarrhoea virus (BVDV).

8. The method according to claim 1 wherein the antigenic polypeptide is expressed in the cell by the introduction into the cell of a polynucleotide encoding the antigenic polypeptide operably linked to a regulatory control sequence capable of directing expression of the polypeptide in the cell.

9. The method according to claim 8 wherein the polynucleotide is part of a virus or viral vector.

10. The method according to claim 9 wherein the cell is an insect cell and the virus or viral vector is a baculovirus or baculovirus vector.

* * * * *

SEQUENCE LISTING

```
<160> NUMBER OF SEQ ID NOS: 12

<210> SEQ ID NO 1
<211> LENGTH: 27
<212> TYPE: DNA
<213> ORGANISM: Artificial sequence
<220> FEATURE:
<223> OTHER INFORMATION: Primer

<400> SEQUENCE: 1
cgcggatcca gtgctggcat ttgaaga                                    27

<210> SEQ ID NO 2
<211> LENGTH: 28
<212> TYPE: DNA
<213> ORGANISM: Artificial sequence
<220> FEATURE:
<223> OTHER INFORMATION: Primer

<400> SEQUENCE: 2
cgcggatccc agactggtgg ccttatga                                   28

<210> SEQ ID NO 3
<211> LENGTH: 28
<212> TYPE: DNA
<213> ORGANISM: Artificial sequence
<220> FEATURE:
<223> OTHER INFORMATION: Primer

<400> SEQUENCE: 3
```

```
cacggatcca gtgcatcaac aacagcct                              28

<210> SEQ ID NO 4
<211> LENGTH: 31
<212> TYPE: DNA
<213> ORGANISM: Artificial sequence
<220> FEATURE:
<223> OTHER INFORMATION: Primer

<400> SEQUENCE: 4
cgcggatcca gttttgtttc aagttacaat g                          31

<210> SEQ ID NO 5
<211> LENGTH: 31
<212> TYPE: DNA
<213> ORGANISM: Artificial sequence
<220> FEATURE:
<223> OTHER INFORMATION: Primer

<400> SEQUENCE: 5
cgcggatcca gttttgtttc aagttacaat g                          31

<210> SEQ ID NO 6
<211> LENGTH: 33
<212> TYPE: DNA
<213> ORGANISM: Artificial sequence
<220> FEATURE:
<223> OTHER INFORMATION: Primer

<400> SEQUENCE: 6
aactgcagac tagagtggtt tgccaaagca aca                        33

<210> SEQ ID NO 7
<211> LENGTH: 28
<212> TYPE: DNA
<213> ORGANISM: Artificial sequence
<220> FEATURE:
<223> OTHER INFORMATION: Primer

<400> SEQUENCE: 7
gcgaagctta ggactctgcg aagtaatc                              28

<210> SEQ ID NO 8
<211> LENGTH: 31
<212> TYPE: DNA
<213> ORGANISM: Artificial sequence
<220> FEATURE:
<223> OTHER INFORMATION: Primer

<400> SEQUENCE: 8
catgccatgg ttaggactct gcgaagtaat c                          31

<210> SEQ ID NO 9
<211> LENGTH: 30
<212> TYPE: DNA
<213> ORGANISM: Artificial sequence
<220> FEATURE:
<223> OTHER INFORMATION: Primer

<400> SEQUENCE: 9
cgcaagctta cgctaccact gccaacatga                            30

<210> SEQ ID NO 10
<211> LENGTH: 28
<212> TYPE: DNA
```

```
<213> ORGANISM: Artificial sequence
<220> FEATURE:
<223> OTHER INFORMATION: Primer

<400> SEQUENCE: 10
cgcaagctta gacatcacag taagggga                                            28

<210> SEQ ID NO 11
<211> LENGTH: 28
<212> TYPE: DNA
<213> ORGANISM: Artificial sequence
<220> FEATURE:
<223> OTHER INFORMATION: Primer

<400> SEQUENCE: 11
cgcaagctta gacatcacag taagggga                                            28

<210> SEQ ID NO 12
<211> LENGTH: 33
<212> TYPE: DNA
<213> ORGANISM: Artificial sequence
<220> FEATURE:
<223> OTHER INFORMATION: Primer

<400> SEQUENCE: 12
acgtccatgg ttaagcttga tagcctacgt acc                                      33
```